United States Patent
Carus et al.

(10) Patent No.: US 7,233,938 B2
(45) Date of Patent: Jun. 19, 2007

(54) SYSTEMS AND METHODS FOR CODING INFORMATION

(75) Inventors: Alwin B. Carus, Waban, MA (US); Stefaan Heyvaert, Cambridge, MA (US); Harry J. Ogrinc, Westwood, MA (US); Robert G. Titemore, Lexington, MA (US); Tom Deplonty, Melrose, MA (US); Keith Boone, Randolph, MA (US); Brian Wilson, Arlington, MA (US); Ray Rankins, Gansevoort, NY (US); Don Fonza, De Pere, WI (US); David Speth, West Seneca, NY (US); Melissa Macpherson, Albuquerque, NM (US)

(73) Assignee: Dictaphone Corporation, Stratford, CT (US)

( * ) Notice: Subject to any disclaimer, the term of this patent is extended or adjusted under 35 U.S.C. 154(b) by 358 days.

(21) Appl. No.: 10/413,405

(22) Filed: Apr. 15, 2003

(65) Prior Publication Data

US 2004/0220895 A1    Nov. 4, 2004

Related U.S. Application Data

(60) Provisional application No. 60/436,456, filed on Dec. 27, 2002.

(51) Int. Cl.
*G06F 17/30* (2006.01)
(52) U.S. Cl. .................... 707/1; 707/2; 707/3; 707/4; 707/5
(58) Field of Classification Search .................... 704/9; 707/1–5; 705/1–3, 34

See application file for complete search history.

(56) References Cited

U.S. PATENT DOCUMENTS

| 4,477,698 A | 10/1984 | Szlam et al. |
| 4,965,763 A | 10/1990 | Zamora |
| 5,253,164 A | 10/1993 | Holloway et al. |
| 5,325,293 A | 6/1994 | Dorne |
| 5,327,341 A | 7/1994 | Whalen et al. |
| 5,392,209 A | 2/1995 | Eason et al. |
| 5,664,109 A | 9/1997 | Johnson et al. |
| 5,799,268 A | 8/1998 | Boguraev |
| 5,809,476 A | 9/1998 | Ryan |
| 5,970,463 A | 10/1999 | Cave et al. |
| 5,974,412 A * | 10/1999 | Hazlehurst et al. ............ 707/3 |

(Continued)

OTHER PUBLICATIONS

Fei Song et al., A Graphical Interface to a Semantic Medical Information System, *Journal of Foundations of Computing and Decision Sciences*, 22(2), 1997.

(Continued)

*Primary Examiner*—Don Wong
*Assistant Examiner*—Sheree Brown
(74) *Attorney, Agent, or Firm*—Kelley Drye & Warren LLP

(57) ABSTRACT

The invention includes a medical document handling system and method and automated coding systems and methods for assigning predetermined medical codes to medical documents based on the documents' contents. The invention functions by analyzing electronic medical records and extracting medical information using natural language processing and machine learning. The system collects and amalgamates medical documentation in various formats from multiple sources and locations, normalizes the information, analyzes the information, recognizes information indicating contents corresponding to classification codes, assigns classification codes, and presents information in context correlated to medical records for billing and other purposes.

10 Claims, 30 Drawing Sheets

U.S. PATENT DOCUMENTS

| | | | |
|---|---|---|---|
| 6,006,221 A * | 12/1999 | Liddy et al. | 707/5 |
| 6,014,663 A | 1/2000 | Rivette et al. | |
| 6,021,202 A | 2/2000 | Anderson et al. | |
| 6,052,693 A | 4/2000 | Smith et al. | |
| 6,055,494 A | 4/2000 | Friedman | |
| 6,088,437 A | 7/2000 | Amick | |
| 6,182,029 B1 * | 1/2001 | Friedman | 704/9 |
| 6,192,112 B1 | 2/2001 | Rapaport et al. | |
| 6,289,353 B1 * | 9/2001 | Hazlehurst et al. | 707/102 |
| 6,292,771 B1 | 9/2001 | Haug et al. | |
| 6,347,329 B1 | 2/2002 | Evans | |
| 6,360,215 B1 * | 3/2002 | Judd et al. | 707/3 |
| 6,405,165 B1 | 6/2002 | Blum et al. | |
| 6,434,547 B1 | 8/2002 | Mishelevich et al. | |
| 6,438,533 B1 | 8/2002 | Spackman et al. | |
| 6,915,254 B1 * | 7/2005 | Heinze et al. | 704/9 |
| 2002/0143824 A1 * | 10/2002 | Lee et al. | 707/523 |
| 2004/0103075 A1 * | 5/2004 | Kim et al. | 707/1 |
| 2004/0243545 A1 | 12/2004 | Boone et al. | |
| 2004/0243551 A1 | 12/2004 | Boone et al. | |
| 2004/0243552 A1 | 12/2004 | Titemore et al. | |
| 2004/0243614 A1 | 12/2004 | Boone et al. | |
| 2005/0108010 A1 | 5/2005 | Frankel et al. | |
| 2005/0114122 A1 | 5/2005 | Uhrbach et al. | |
| 2005/0120020 A1 | 6/2005 | Carus et al. | |
| 2005/0120300 A1 | 6/2005 | Schwager et al. | |
| 2005/0144184 A1 | 6/2005 | Carus et al. | |

OTHER PUBLICATIONS

Fei Song et al., A Cognitive Model for the Implementation of Medical Problem Lists, *Proceedings of the First Congress on Computational Medicine, Public Health and Biotechnology*, Austin, Texas, 1994.

Fei Song et al., A Graphical Interface to a Semantic Medical Information System, *Karp-95 Proceedings of the Second International Symposium on Knowledge Acquisition, Representation and Processing*, pp. 107-109, 1995.

Epic Web Training Manual, pp. 1-33, 2002.

B. Hieb, Research Note, NLP Basics for Healthcare, Aug. 16, 2002.

C. Shalizi et al., Pattern Discovery in Time Series, Part I: Theory, Algorithm, Analysis, and Convergence, *Journal of Machine Leaning Research* ? (2002) ?-? Submitted Oct. 28, 2002; Published ?/2002.

C. Nevill-Manning et al., The Development of Holte's 1R Classifier, Department of Computer Science.

D. Cutting et al., A Practical Part-of-Speech Tagger, Xerox Palo Alto Research Center.

J. Zavrel et al., Recent Advances in Memory-Based Part-of-Speech Tagging, ILK/Computational Linguistics.

E. Brill, Some Advances in Transformation-Based Part of Speech Tagging, Spoken Language Systems Group.

J. Nivre, DAC723: Language Technology Finite State Morphology, Vaxjo University of Mathematics and Systems Engineering, p. 1/11.

M. Creutz, Morphology and Finite-State Transducers, Oct. 31, 2001, Chap 3, Jurafsky & Martin.

http://www.comp.lancs.ac.uk/computing/research/stemming/general/index.htm printed Jul. 19, 2004.

http://www.comp.lancs.ac.uk/computing/research/stemming/general/stemmingerrors.htm printed Jul. 19, 2004.

http://www.comp.lancs.ac.uk/computing/research/stemming/general/performance.htm printed Jul. 19, 2004.

M. Lee et al., Cleansing Data for Mining and Warehousing, Lecture Notes in Computer Science vol. 1677 archive, *Proceedings of the 10th International Conference on Database and Expert Systems Applications*, pp. 751-760, Springer-Verlag, London, 1999.

C. Van Rijsbergen, *Information Retrieval*, 2nd Ed., Ch. 5, Butterworths, London, 1979.

J. Day, Extracting Knowledge from Text Using Learning by Constraint Relaxation (LCR), CSI, www.csi-inc.com/CSI/pdf/jday_icim02.pdf.

W. Gale et al., Discrimination Decisions for 100,000-Dimensional Spaces, *Current Issues in Computational Linguistics*, pp. 429-450, Kluwer Academic Publishers, 1994.

W. Daelemans et al., TiMBL: Tilburg Memory Based Learner, version 5.0, Reference Guide, ILK *Research Group Technical Report Series No. 04-02* (*ILK-0402*), ILK Research Group, Tilburg University, Tilburg, Netherlands, 2004.

Case Study: Massachusetts Medical Society http://www.microsoft.com/resources/casestudies/CaseStudy.asp?CaseStudyID=14931 posted Jan. 13, 2004.

W. Braithwaite, Continuity of Care Record (CCR) http://www.hl7.org/library/himss/2004Orlando/ContinuityofCareRecord.pdf.

C. Waegemann, *EHR* vs. *CCR*: What is the difference between the electronic health record and the continuity of care record?, Medical Records Institute, 2004.

Press Release: Kryptiq Announces Support of CCR Initiative and Introduces New Solutions that Enable Information Portability, Accessibility and Clinical System Interoperability, http://www.kryptiq.com/News/PressReleases/27.html posted Feb. 17, 2004.

Work Item Summary: WK4363 Standard Specification for the Continuity of Care Record (CCR), http://www.astm.org/cgi-bin/SoftCart.exe/DATABASE.CART/WORKITEMS/WK4363.htm?E+mystore Mar. 3, 2004.

Continuity of Care Record (CCR): The Concept Paper of the CCR, v. 2.1b, http://www.bhtinfo.com/CCR.Concept%20Paper.1.5.doc.

Continuity of Care Record, American Academy of Family Physicians, http://www.aafp.org/x24962.xml?printxml posted Nov. 12, 2003.

Continuity of Care Record (CCR), AAFP Center for Health Information Technology, http://www.centerforhit.org/x201.xml posted Aug. 20, 2004.

Core Measures web page, Joint Commission on Accreditation of Healthcare Organizations, http://www.jcaho.org/pms/core+measures/ printed Mar. 22, 2004.

*Specifications Manual for National Implementation of Hospital Core Measures*, v. 2.0, Joint Commission on Accreditation of Healthcare Organizations, http://www.jcaho.org/pms/core+measures/information+on+final+specifications.htm.

Code Information and Education web page, American Medical Association, http://www.ama-assn.org/ama/pub/category/3884.html printed Mar. 22, 2004.

Category III CPT Codes, American Medical Association, http://www.ama-assn.org/ama/pub/article/3885-4897.html printed Mar. 22, 2004.

ICD-9-CM Preface (FY04), http://ftp.cdc.gov/pub/Health_Statistics/NCHS/Publications/ICD9-CM/2004/Prefac05.RTF.

*ICD-9-CM Official Guidelines For Coding and Reporting*, effective Oct. 1, 2003.

Q. X. Yang et al., "Faster algorithm of string comparison," *Pattern Analysis and Applications*, vol. 6, No. 1, Apr. 2003: pp. 122-133.

"Hardware Reference Manual," Release 3 for DOS, revised Jan. 1994, PIKA Technologies, Inc., Ontario, Canada, available at http://www.pikatechnologies.com/downloads/legacy/AVA%20B-Series%20Hardware%20Manual.pdf (last accessed Jul. 25, 2005).

"Customizing D/41 Call Analysis," date unknown, Intel Corp., Santa Clara, California, available at http://resource.intel.com/telecom/support/appnotes/custd41d.htm (last accessed Jul. 25, 2005).

U.S. Appl. No. 11/068,493, Carus, et al.

U.S. Appl. No. 10/953,471, Cote, et al.

U.S. Appl. No. 11/069,203, Cote, et al.

U.S. Appl. No. 11/007,626, Cote, et al.

U.S. Appl. No. 10/840,428, Carus, et al.

U.S. Appl. No. 10/951,281, Cote, et al.

\* cited by examiner

IIC Web Application

*(305)* *(310)* ichart  
Coding  
[Previous] [Retail]

MRN: 1176848  
Visit ID: 1176848  
Patient ID:  
Admit Date: 09/18/01  
Discharge Date:  
Patient SSN:

[View Source]  
[Help]

*(320)*

Number of documents found for this encounter: 9

LC#: 1176848

ADMISSION DATE: 09/17/01

DISCHARGE DATE: / /

REFERRING PHYSICIAN: John F Beamis Jr, MD

REASON FOR CONSULTATION:
Methicillin-resistant Staphylococcus aureus (MRSA) sepsis.

HISTORY: 6 The patient was admitted on September 17, 2001 for further evaluation of methicillin-resistant Staphylococcus aureus bacteremia. The patient has a long, complicated history with many years of osteoarthritis and has had multiple surgical procedures on her back, knees and most recently on her right shoulder. She has a prosthesis in her right shoulder and her left knee.

PAST:
This patient also has a past medical history of left lower lobe pneumonia with MRSA, chronic obstructive pulmonary disease (COPD), osteoarthritis, history of pancreatitis, history of anemia of chronic disease, hypertension status post right shoulder and left knee replacement, cervical myopathy and peptic ulcer disease.

CURRENT MEDICATIONS: Include Colace, Dilaudid, Prevacid, Reglan, vancomycin, 1 gm q.12h. started on September 18, 2001; Macrobid, prednisone, Duragesic, Duragesic patch, Norvasc, Flovent, Serevent, verapamil SR, Combivent, diazepam, Prozac, Compazine, Tylenol, Celebrex.

*(330)*

*(340)*

Diagnosis
- 038.9
- 278.00
- 305.1
- 401.9
- 424.90  — ENDOCARDITIS NOS
  - PD_09-18-01_Consults
  - PD_09-18-01_Consults
  - PD_09-18-01_Consults
  - PD_09-18-01_Consults
  - PD_09-18-01_Consults
  - PD_09-18-01_Consults
  - PD_09-18-01_Consults
  - PD_09-18-01_Consults
  - PD_09-18-01_Consults
  - PD_09-18-01_Consults
  - PD_09-18-01_Consults
  - PD_09-18-01_Consults
  - PD_09-18-01_Consults
  - PD_09-18-01_Consults

*(350)* *(335)*

Dictaphone

FIGURE 3

SYSTEMS AND METHODS FOR CODING INFORMATION

CROSS-REFERENCE TO RELATED APPLICATION

This application claims the benefit of priority of U.S. Provisional Patent Application No. 60/436,456, entitled "SYSTEMS AND METHODS FOR CODING INFORMATION," filed Dec. 27, 2002, which is hereby incorporated by reference in its entirety. This application relates to co-pending U.S. patent application Ser. No. 10/447,290, entitled "SYSTEM AND METHODS UTILIZING NATURAL LANGUAGE PATIENT RECORDS," filed on May 29, 2003; co-pending U.S. patent application Ser. No. 11/068,493, entitled "A SYSTEM AND METHOD FOR NORMALIZATION OF A STRING OF WORDS," filed on Feb. 28, 2005; co-pending U.S. patent application Ser. No. 10/448,320, entitled "METHOD, SYSTEM, AND APPARATUS FOR DATA REUSE," filed on May 30, 2003; co-pending U.S. patent application Ser. No. 10/787,889, entitled "SYSTEM, METHOD AND APPARATUS FOR PREDICTION USING MINIMAL AFFIX PATTERNS," filed on Feb. 27, 2004; co-pending U.S. patent application Ser. No. 10/448,317, entitled "METHOD, SYSTEM, AND APPARATUS FOR VALIDATION," filed on May 30, 2003; co-pending U.S. patent application Ser. No. 10/448,325, entitled "METHOD, SYSTEM, AND APPARATUS FOR VIEWING DATA," filed on May 30, 2003; co-pending U.S. patent application Ser. No. 10/953,448, entitled "SYSTEM AND METHOD FOR DOCUMENT SECTION SEGMENTATIONS," filed on Sep. 30, 2004; co-pending U.S. patent application Ser. No. 10/953,471, entitled "SYSTEM AND METHOD FOR MODIFYING A LANGUAGE MODEL AND POST-PROCESSOR INFORMATION," filed on Sep. 29, 2004; co-pending U.S. patent application Ser. No. 10/951,291, entitled "SYSTEM AND METHOD FOR CUSTOMIZING SPEECH RECOGNITION INPUT AND OUTPUT," filed on Sep. 27, 2004; co-pending U.S. patent application Ser. No. 10/953,474, entitled "SYSTEM AND METHOD FOR POST PROCESSING SPEECH RECOGNITION OUTPUT," filed on Sep. 29, 2004; co-pending U.S. patent application Ser. No. 10/951,281, entitled "METHOD, SYSTEM AND APPARATUS FOR REPAIRING AUDIO RECORDINGS," filed on Sep. 27, 2004; co-pending U.S. patent application Ser. No. 11/069,203, entitled "SYSTEM AND METHOD FOR GENERATING A PHASE PRONUNCIATION," filed on Feb. 28, 2005; co-pending U.S. patent application Ser. No. 11/007,626, entitled "SYSTEM AND METHOD FOR ACCENTED MODIFICATION OF A LANGUAGE MODEL," filed on Dec. 7, 2004; co-pending U.S. patent application Ser. No. 10/948,625, entitled "METHOD, SYSTEM, AND APPARATUS FOR ASSEMBLY, TRANSPORT AND DISPLAY OF CLINICAL DATA," filed on Sep. 23, 2004; and co-pending U.S. patent application Ser. No. 10/840,428, entitled "CATEGORIZATION OF INFORMATION USING NATURAL LANGUAGE PROCESSING AND PREDEFINED TEMPLATES," filed on Sep. 23, 2004, all of which are hereby incorporated by reference in their entirety.

BACKGROUND OF THE INVENTION

Hospitals, medical clinics, medical offices, and other sources of medical care typically keep records for their patients. These records include a variety of information such as doctors' notes regarding the patients' complaints and symptoms, diagnoses, notes regarding treatments and procedures administered, patients' drug or other allergies, medicines the patient has been taking, and medicines that are newly prescribed. A great deal of information is thus generated for each patient, and in hospital or clinical environments, where numerous patients are treated, the volume of information generated for all patients can become truly enormous, thus creating an ever present need for more efficient ways of handling the information.

One of the ways that the healthcare industry has developed to manage healthcare information involves the standardization of nomenclature for diagnoses, treatments, medical procedures, medications, and other medical services. Many systems of standardization exist. One system is the International Classification of Diseases (ICD-9, which indicates the $9^{th}$ revision), published by the World Health Organization. The International Classification of Diseases is a classification structure that provides rules for assigning numeric codes that specify causes of death for death certificates, thus facilitating analysis of mortality statistics. The Center for Disease Control (CDC) has expanded the ICD-9 to include classification codes for diagnoses and procedures for hospitals in the United States. The ICD-9-CM thus provides a clinical modification (CM) to the ICD-9 that includes codes for surgical, diagnostic, and therapeutic procedures, as well as the disease codes of the ICD-9. A recent revision of the ICD, ICD-10 (1999), expands the list of disease codes. The CDC anticipates release of a revision of its clinical modification and has made a draft version of the ICD-10-CM available for review, but no other purposes. Currently only the codes of the ICD-9-CM are in use.

Other systems of medical classification include the Current Procedural Terminology (CPT), published by the American Medical Association (AMA). The CPT provides classification codes for medical diagnoses to provide a uniform language for medical services including surgical, radiological, diagnostic, and therapeutic services, as well as codes for services provided in various medical specialties and laboratory procedures. Another classification system is the Systemized Nomenclature of Medicine (SNOMED), published by the College of American Pathologists (CAP). SNOMED provides detailed and specific classification codes for clinical information and reference terminology and is cross-referenced to the ICD.

Notwithstanding the variety of options available for standardization of medical records, physicians and other healthcare providers rarely use classification codes in creating medical records because classification usually involves significant effort and is not worth the physicians' time. However, healthcare providers are often required to provide standardized medical reports in order to recover expenses from insurance providers. Furthermore, the medical community can benefit from standardized medical records for such purposes as statistical analyses of disease and epidemic containment. Thus healthcare providers typically employ coding specialists, who review patients' medical records, extract information regarding medical services provided, manually look up the classification codes for those services, and annotate the medical record with the codes corresponding to the services provided. These annotated medical records are then provided to insurers for payment for services provided.

One problem that plagues this system is the coding specialists' failure to find all billable services and to provide codes corresponding to those services to insurers. This failure can result in loss of significant revenue to the medical facility. There is therefore a need for a more reliable system of assigning codes to medical records. Coding specialists can benefit from a more complete picture of a patient's medical record, yet they are often asked to analyze a patient's medical history piecemeal, as particular treatments are administered. There is therefore a need for a system which can gather and assemble various documents from various sources within a medical facility in order to provide a more complete picture of that patient's treatment.

An option for increasing the reliability of coding is to add automation to the process. Automated coding systems do exist, the most famous of such systems known as the Gabrieli engine was developed by Dr. Elemér Gabrieli. The Gabrieli engine is a coding engine—a text processor for parsing free medical text, such as that written or dictated by a physician while diagnosing or treating a patient, and translating it into a system of medical codes. The Gabrieli engine sorts through the input medical text, rearranging and tweaking it, searching for a reasonable match of the input medical text to a database of predetermined medical descriptions corresponding to particular classification codes. The Gabrieli engine was revolutionary for its time, but it has significant shortcomings, such as its relatively slow speed, its relative inaccuracy, and its relative inability to learn from prior coding failures. There is therefore a need for improved automated coding systems.

SUMMARY OF THE INVENTION

The present invention provides systems and methods for improved coding. In one aspect, the invention provides a system and method for amalgamating documents from various sources into a single master document. In another aspect, the invention includes a system and method for document and workflow handling of medical texts for coding. In another aspect, the invention includes a system and method for formatting documents into a uniform format for facilitating analysis of the document. In another aspect, the invention includes an improved system and method for automated coding of documents. In another aspect, the invention includes a system and method for providing feedback to automated coding engines to improve automated coding performance. In another aspect, the invention includes a system and method for presenting documents with coding.

In one embodiment, the invention includes a method for processing any type of file that needs any type of processing. In this embodiment, the method includes receiving a file to be processed in a monitored directory on a file server; creating job information from information in the file to be processed or from predetermined information based on the identity of the monitored directory; storing the job information in a database; performing at least one operation on the file to be processed, thereby creating a processed file, wherein the at least one operation performed is determined from the job information stored in the database. In one embodiment, the processed file may be stored in a client database. The files that may be processed according to this method include audio files, voice files, video files, picture files, and text files. In one embodiment, the method includes processing medical records. The medical record processing operations include medical coding. In this aspect of the invention, the medical codes may be justified by text in the file to be processed.

In another embodiment, the invention includes a system for processing any type of file that needs any type of processing. In this embodiment, the system includes a file server for receiving a file to be processed in a monitored directory; an application for creating job information from information in the file to be processed or from predetermined information based on the identity of the monitored directory; a job database wherein the job information is stored in the job database; an application for performing at least one operation on the file to be processed, thereby creating a processed file, wherein the at least one operation performed is determined from the job information stored in the database. In one embodiment, the processed file may be stored in a client database. The files that may be processed using this system include audio files, voice files, video files, picture files, and text files. In one embodiment, the system may be used to process medical records. The medical record processing operations include medical coding. In this aspect of the invention, the medical codes may be justified by text in the file to be processed.

In another embodiment, the invention includes a method for medical document coding. In this embodiment, the method includes receiving medical documents for coding from multiple clients, wherein the medical documents from each client are received in client-specific directories on a file server; normalizing the form of the documents in a predetermined format, wherein the predetermined format is determined from information in the file or from which directory on the file server the medical documents are received; normalizing the content of the documents; identifying coded items, wherein the coded items are determined based on the text in the medical documents; filtering the coded items, wherein the coded items are filtered based on a probabilistic filter with predetermined probabilities; creating a coded document, wherein the coded document contains text justifying the filtered coded items, and the filtered coded items. In one embodiment, the coded document may be stored in a client database. In one embodiment, the method may further include post-processing the coded document. In another embodiment, the normalizing step may include converting the document to XML format.

In another embodiment, the invention includes a system for medical document coding comprising a file server for receiving medical documents for coding from multiple clients, wherein the medical documents from each client are received in client-specific directories on the file server; an application for normalizing the form of the documents in a predetermined format, wherein the predetermined format is determined from information in the file or from which directory on the file server the medical documents are received; an application for normalizing the content of the documents; a coding engine for identifying coded items, wherein the coded items are determined based on the text in the medical documents; an application for filtering the coded items based on a probabilistic filter with predetermined probabilities; an application for creating a coded document, wherein the coded document contains text justifying the filtered coded items, and the filtered coded items. In another embodiment, the coded document may be stored in a client database. In one embodiment, the coding engine may be a Gabrieli engine. In another embodiment, the invention may include an application for post-processing the coded document. In another embodiment, the application for normalizing the form of the document may convert the document to XML format. In another embodiment, the coding engine may provide ICD-9-CM codes.

BRIEF DESCRIPTION OF THE DRAWINGS

While the specification concludes with claims particularly pointing out and distinctly claiming the present invention, it is believed the same will be better understood from the following description taken in conjunction with the accompanying drawings, which illustrate, in a non-limiting fashion, the best mode presently contemplated for carrying out the present invention, and in which like reference numerals designate like parts through the figures, wherein:

FIG. 3 shows an example of a web-based viewing application for viewing the results of a coded document;

DETAILED DESCRIPTION

Figure 1:
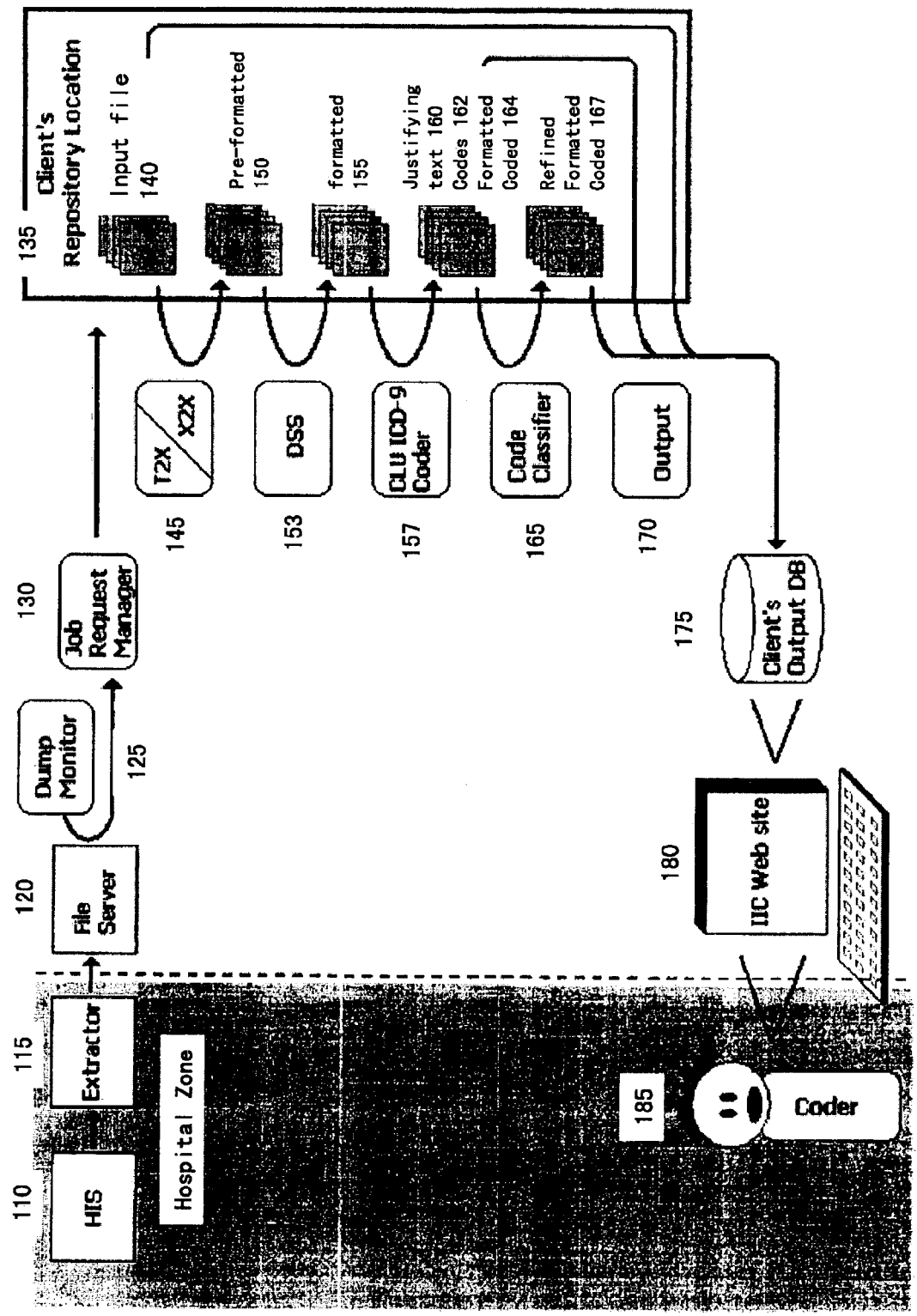
FIG. 1 is a block diagram illustrating components of a system according to one embodiment of the invention.
Figure 2:
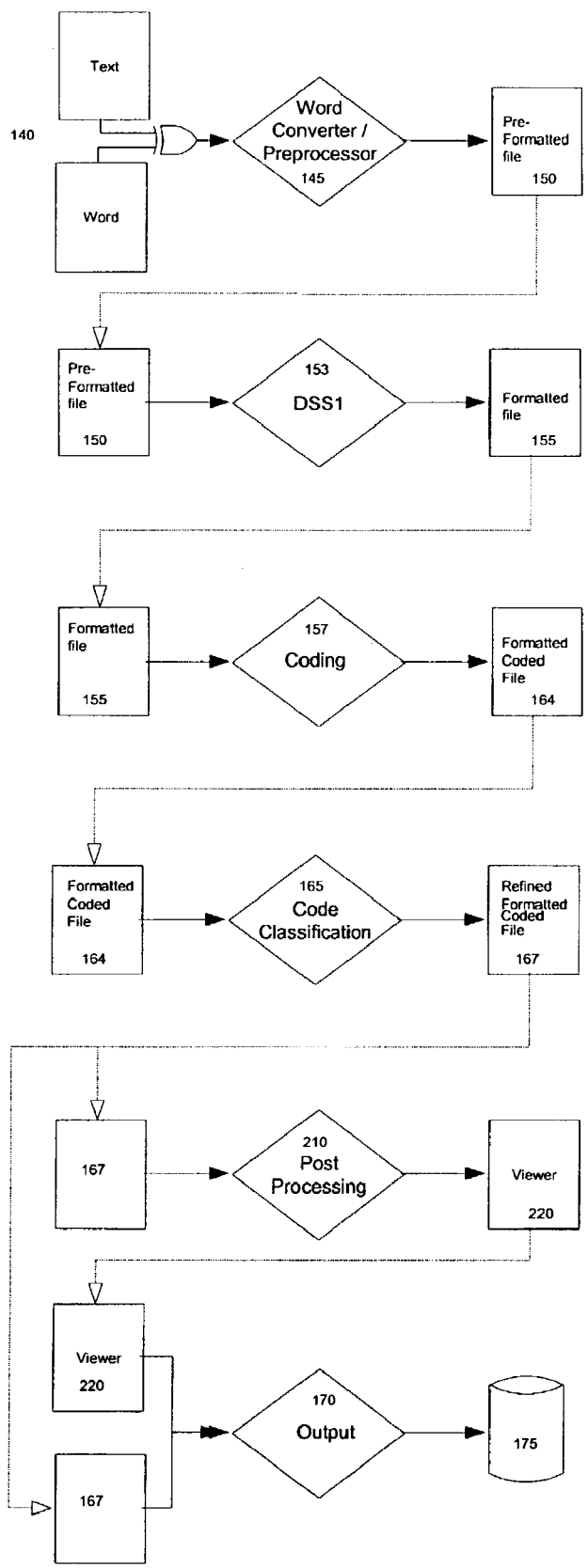
FIG. 2 is a flow diagram illustrating steps of one of the methods according to one embodiment of the invention.

An overview of one embodiment of the system of the invention is illustrated in FIG. 1, and one of the methods of the invention that may be performed on this system is illustrated in FIG. 2. A hospital, clinic, or other medical services facility (herein after "hospital") may maintain an electronic database of patient records 110. The patient records may be comprised of single files containing entire records for each patient, or the record for each patient may be comprised of individual files corresponding to the individual departments of the hospital from which the patient received services. Any other suitable format for the patient records may be used with the invention. In one embodiment, the invention includes a compiling software program running on a hospital server or an outside server, wherein the compiling software program gathers individual files corresponding to individual departments of the hospital from which a single patient has received services, and assembles the data from each of the individual files into a single master patient record. The information from each of the individual files may be inserted into the single master patient record according to predetermined rules for organizing the information. In a preferred embodiment, all of the files generated during a patient's visit to a hospital are compiled into a single master patient encounter record, with different master patient encounter records generated for each visit a patient makes to a hospital. This preferred embodiment is particularly preferred for the creation of master patient encounter records for inpatient hospital services.

A software extractor program 115 may run on a hospital server. The extractor program 115 may extract files from the hospital database 110 of patient record files. The extractor program may select files to be extracted based on such criteria as the files' locations, their dates of creation, or because the files have been manually selected. When the extractor program 115 selects a file it may send the file over a communications network to a centrally located file server 120 that forms part of a job management system. The file server 120 may be configured to receive files from many different hospitals. Preferably, the file server 120 is configured such that files from different hospitals are saved in different receiving directories, where each receiving directory is designated to receive files from a corresponding hospital.

A software dump monitor program 125 may run on a server in the job management system. The dump monitor 125 may monitor the file server 120 to determine whether any new files have been deposited in any of the receiving directories thereon. When the dump monitor 125 detects the presence of a new file on the file server 120, it may make minor modifications to the file to indicate which directory on the file server 120 the file was found, thus indicating which hospital sent the file. The dump monitor 125 may also modify the file to indicate what processing should be done to the file based on which directory or subdirectory on the file server 120 the file was found or based on any other appropriate indicator including, for example, the file content. Dump monitor 125 may then transfer control of the file to another software program, the job request manager 130, running on the same or another server in the job management system.

The job request manager 130 may search the file for a predetermined indication that the file should be processed for coding. The predetermined indication may have been placed in the file by dump monitor 125 based on the file location on file server 120, or based on some other appropriate indicator. When job request manager 130 determines that a file has been designated to be processed for coding, it sends the file to a repository server 135. The repository server 135 may in general be the same or a different server than the file server 120, the server on which the dump monitor program 125, or the job request manager 130 run.

An input file 140 placed on the repository server 135 may be processed in a number of different ways. The file may be converted to XML into a standard format by a text-to-XML converter, thereby producing a preformatted file 150. The input file 140 need not necessarily be in simple text format, but may be in any format used by the hospital at which it was generated. Furthermore, XML is not a necessary part of the invention; any suitable format including simple text or any suitable markup language may be used. File format conversion utilities are for converting files from almost any format to almost any other format are commonplace and well-known to those skilled in the art. For the sake of describing the invention, it will be assumed that the documents are manipulated in XML format. The preformatted file 150 is then further processed by a document segmentation service (DSS) software program 153, which identifies sections and headings in preformatted file 150, and adds identifiers, for example XML markups, to mark the sections and headings, thereby creating a formatted file 155.

A coding engine 157 may be applied to the formatted file 155. The coding engine may suggest codes justified by the text of the formatted file 155. In general, the coding engine 157 may suggest any type of codes suitable for identifying text within the formatted file 155. For example, the coding engine 157 may suggest ICD-9 codes, ICD-10 codes, ICD-9-CM codes, ICD-10-CM codes, SNOMED codes, CPT codes, or any other standardized classification system for identifying the possible meaning of the text of the formatted file 155. The coding engine 157 may be, for example, a Gabrieli engine or any other coding engine known in the art. Preferably, however, the coding engine 157 is the coding engine of the invention as described herein. The coding engine 157 may generate three output files: (1) a justifying text file 160 containing the text within the formatted file 155 that justifies the selection of the particular codes suggested, (2) a codes file 162 containing the codes that have been selected based on the text in the formatted file 155, and particularly on the text from the formatted file set forth in the file 160, and (3) a formatted coded file 164 containing the original text of the formatted file 155 and the codes that have been selected based on the text in the formatted file 155. Preferably, the formatted coded file 164 is an XML file that is marked up such that the selected codes are linked to the portions of text which justifies the selected codes. In general, however, the formatted coded file 164 may be in any format suitable for associating codes with portions of text found to justify those codes.

A code classifier program 165 may be applied to the coded file 164 to produce a refined formatted coded file 167. The code classifier 165 may refine the coded file 164 by eliminating some of the codes that were suggested by the coding engine 157. The code classifier 165 may contain filters that recognize particular codes that are irrelevant for particular purposes. For example, files from a particular source, such as a dermatologist's office, may include text that suggests a code indicating treatment for high blood pressure, which the coding engine 157 picks up on and suggests a code for that treatment. However, the code classifier 165 may recognize that the source of the file is a dermatologist's office, and may restrict the allowable codes to those treatments that are relevant to dermatology. In general, the code classifier may contain one or more site-specific probabilistic filters, wherein each hospital that saves files on the file server 120 has a corresponding site specific probabilistic filter that is applied to each of the files that particular hospital saves on the file server 120.

Alternatively, the code classifier 165 may contain probabilistic filters that are specific to particular parts of a document or particular types of document in addition to or instead of being site specific. For example, one part of a patient record may indicate surgical procedures performed on the patient, and another part of the same patient record may indicate pharmaceuticals prescribed to the patient. A document-part-specific probabilistic filter would discount the probability that, for example, "heart treatment" means heart surgery if it appears in the medication section, but would increase the probability of that meaning if it appears in the surgical procedures section.

When all of the processing steps have been performed to generate a refined formatted coded file 167 from an input file 140, an optional post-processing step 210 (See FIG. 2) may convert the refined formatted coded file 167 into a format that is compatible with viewing software. An output generator program 170 gathers one or more of the files that have been processed or were the result of the processing steps. Preferably, the output generator 170 gathers the input file 140, the formatted coded file 164, and the refined formatted coded file 167, and saves these files to an output database 175. Preferably, a separate output database exists for each of the clients who sends files to the file server 120. In a preferred embodiment, the output database includes a directory on a server, wherein a separate directory exists for each hospital.

Within a hospital, a human coding specialist 185 may access the output database 175 via a web site 180 through a communications network. The coding specialist may simply accept the results of the refined formatted coded file 167, and pass the codes contained in this file along for insurance billing or other purposes. Alternatively, the coding specialist may simply accept the results of the formatted coded file 164, which would likely contain more codes than the refined formatted coded file 167. In a preferred embodiment, the coding specialist may review the contents of the refined formatted coded file 167 and verify that each of the codes contained therein is justified by the corresponding text, and that every code that is properly justified by the text is contained in the refined coded file. In alternative embodiments, the coding specialist may review the contents of the formatted coded file 164 and verify that each of the codes contained therein is justified by the corresponding text, and that every code that is properly justified by the text is contained in the refined formatted coded file 167.

In still another embodiment, the coding specialist 185 may review either the formatted coded file 164, the refined formatted coded file 167, or both, and may provide feedback in the form of missed codes or of codes that were improperly added to the files. The feedback may then be used to modify the probabilistic filter corresponding to the hospital that employs the coding specialist 185, or it may be used to modify the model used by the coding engine 157 to assign codes to text. For example, if a coding specialist finds that a particular string of text justifies a code that has not been assigned, the coding specialist may select that string of text, specify what code should be assigned to that string, and provide feedback in the form of that string and the code that should be assigned. The model used by the coding engine 157 may then be updated to reflect the fact that when that particular string of text or a similar string of text is present in future documents, it should assign the specified code.

Alternatively, if a coding specialist finds that a particular code in a refined formatted coded file 167 or a formatted coded file 164 contains a code that is not properly justified by the text, the coding specialist may indicate as much and the model used by the coding engine 157 may be adjusted such that the string that was used to identify that code no longer identifies that code. Alternatively, if a coding specialist 185 finds that a particular code may be justified by a string of text, but that the code is irrelevant to the particular practice area of the hospital employing the coding specialist 185, the coding specialist 185 may specify that the code is irrelevant. The code classifier 165 may then update its probabilistic filter for the hospital employing that coding specialist to indicate that the particular code is less probable from that hospital.

Referring now to FIG. 3, there is an example of a web-based application that can be used with the invention to view the formatted coded files 164 and refined formatted coded files 167 generated by the systems and methods of the invention. The application can be viewed using any suitable internet browser program 305 such as Netscape Navigator® or Microsoft® Internet Explorer®. The application may provide summary information 310 extracted from the file being viewed that identifies the patient and the dates the patient was admitted and discharged, for example. The application may also provide information 320 about how many files were joined to create the file being viewed. For example, if the patient visited nine various departments within the hospital during a particular inpatient visit, and each of the nine departments generated a separate file for the patient regarding diagnoses and medical services provided, then the system may compile all of the information into a single file that is analyzed as described above. The file may then indicate that it contains information compiled from nine different documents 320.

In the left-hand window 330, the viewer may display the text of the formatted file with the information extracted from each of the component files arranged under predetermined headers. In the right-hand window 335, the viewer may display the codes 340 that have been assigned to the document using the systems and methods of the invention, as described above. Each of the codes 340 can be expanded 350 to provide additional information about the code, such as the text within the file that justifies the code. The viewer may also have options for providing additional codes that may have been missed by the coding system of the invention, and for sending these additional codes back to the job management system so that improvements can be made to the coding system.

Figure 4:
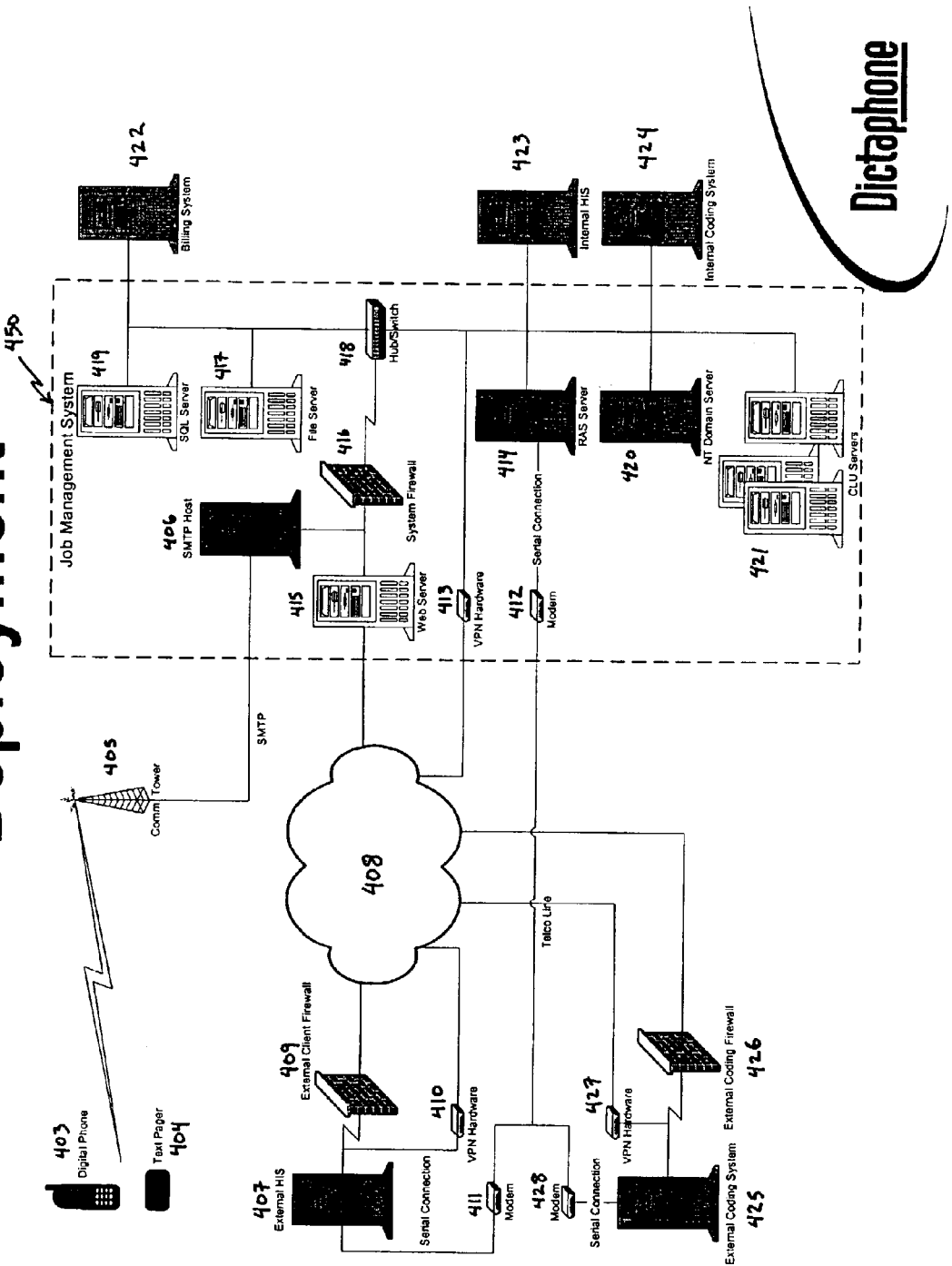
FIG. 4 is a schematic diagram illustrating components of a system according to one embodiment of the invention.

FIG. 4 shows a schematic diagram illustrating major components of a system according to one embodiment of the invention. In one aspect, the system may include a means for receiving instructions from remote communications devices such as digital phones 403 or pager 404 through a communications tower 405 to a simple mail transfer protocol (SMTP) host computer 406. The system may include an external client-side server 407 for storing patient records or other files to be processed. The external client-side server may be connected to the internet 408 through an external firewall 409 or through virtual private networking (VPN) hardware 410. Alternatively, or additionally, the client-side server may be connected to the system through a modem 411.

The job management system (JMS) 450 may include a network of computers connected through a web server 415 and firewall 416 or through VPN hardware 413 to the internet 408. Alternatively or additionally, the JMS may be connected directly to a client-side server 407 via a modem 412 connected to a remote access server (RAS). The JMS 450 may further include one or more structured query language (SQL) database servers 419, file servers 417, domain servers 420, and specialized servers 421 for running system software. The JMS may additionally be connected to one or more internal servers for billing 422, information storage 423, and performing operations such as coding 424. Results from processing by the JMS and internal servers may be accessible to a client-side coding system 425, for example, by connection to the internet 408 through a firewall 426 or a VPN 427, or though a modem connection 428.

FIGS. 5–13 detail the steps in a method of the invention for processing files. The dashed lines represent data flow into and out of various databases, tables, or other information repositories. Solid lines represent the flow of control between the various steps in each process. For purposes of explanation only, the files shown in the description of this method are medical records. However, it should be recognized that any type of file that may require any sort of processing may be processed according to the method of the invention as described herein. Thus, for example, audio files, voice files, video files, picture files, or text files may be processed according to the methods of the invention.

Figure 5:
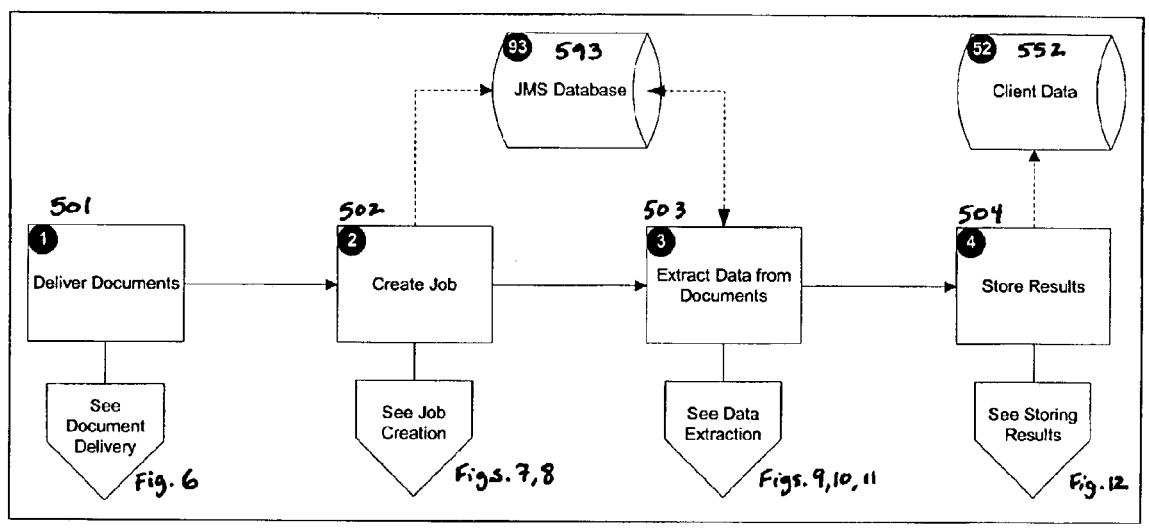
FIG. 5 is a flow diagram showing steps of a method according to one embodiment of the invention.

FIG. 5 shows the main steps of the method according to one embodiment of the invention. In step 501, medical records may be delivered to the job management system (JMS) by depositing them in monitored directories located on a file server. The records may be aggregated into a single file using text delimiters or other file archiving mechanisms. The document delivery subsystem may marshal the individual files to another monitored directory and create a job request, as detailed below in the description of FIG. 6. Any file repository that generates a notification when new information is added to the repository may be used with the document delivery subsystem.

In step 502, a job creation subsystem picks up the job request, parses it, and creates a job. Job information is stored in the JMS database 593, which is accessible to all software components of the JMS system. The JMS database 593 may contain information related to queuing of jobs, the identity of clients and licensing information, the structure of applications deployed using the JMS, and the current status of software programs that supply processing for the applications. The job creation steps are detailed in FIGS. 7 and 8.

In step 503, the software programs that provide extraction services may process the medical records by picking up service requests from the JMS database 593. The extraction steps are detailed in FIGS. 9, 10, and 11.

In step 504, the information that has been extracted from the medical records can be marshaled to other applications outside of the JMS, for example, the extracted information may be stored in a client database 552. The information storing steps are detailed in FIG. 12.

Figure 6:
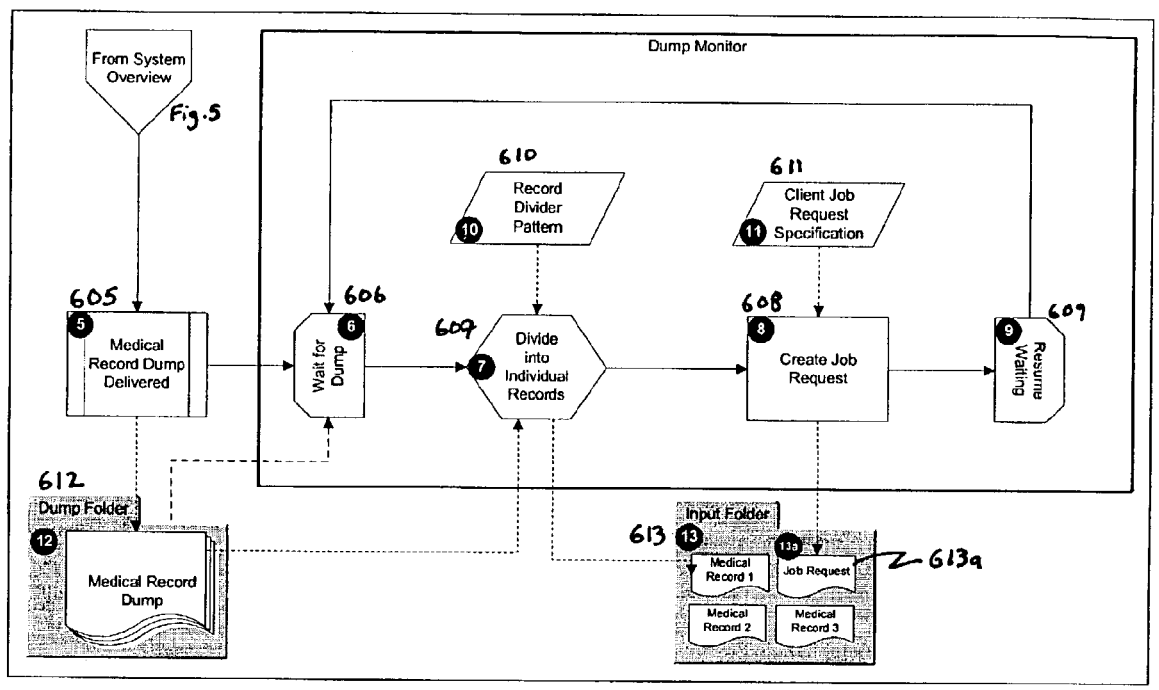
FIG. 6 is a flow diagram detailing document delivery steps according to one embodiment of the invention.

FIG. 6 shows the details of the steps involved in document delivery 501. The document delivery subsystem may receive information provided by outside computer systems, divide the files received into their constituent components, and create an XML document that describes the processing to be performed on the constituent components. The document delivery subsystem may be a service or daemon process, and may use the service control flow detailed in FIG. 13.

In step 605, medical record dumps may be delivered by external computer systems that integrate with the JMS by sending files to a repository, or a dump folder 612. The dump folder 612 sends an event notification to a dump monitor that may be waiting for a new dump to indicate that a medical record dump has been delivered. Delivery systems include, but are not limited to, FTP, HTTP, delivery by storing files in a directory on a file server, or other mechanisms. When the dump monitor receives an event notification 606, it triggers the processing.

In step 607, the file may be broken up into individual documents based on the a record divider pattern 610 stored in the JMS database 593. The record divider pattern may specify how the files should be separated, which may include mechanisms such as text pattern matching or de-archiving, for example from a zip or tar file. If the record divider pattern is empty, the dump monitor may simply deliver the file as a single unit. Files may be copied to the input folder 613.

In step 608, the dump monitor may use the client job request specification 611, which may be stored in the JMS database 593, to determine what type of job request to submit. It may then construct a job request 613a, which may be stored in the input folder 613. The job request 613a may provide information about the application to use for processing, the client who is requesting the processing, and the files that are to be processed.

In step 609, the dump monitor has completed its task for the present dump, and it may then return to step 605, and thus resume waiting for a subsequent dump. In order to prevent missing an event notification from a subsequent dump receipt while the dump monitor is engaged in processing a medical record, it is preferable to provide a queue for event notifications for the dump monitor. Modem operating systems including Windows and Unix provide event queues.

Figure 7:
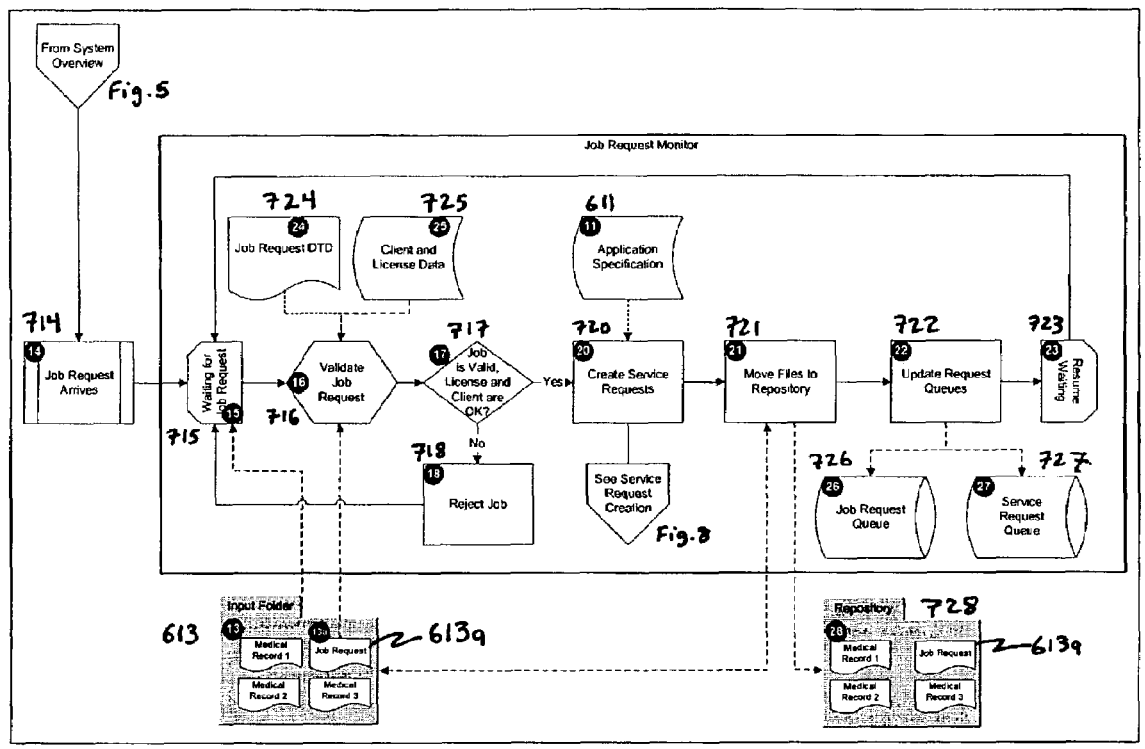
FIG. 7. is a flow diagram detailing job creation steps according to one embodiment of the invention.

FIG. 7 shows the details of the steps involved in job creation 502. A job request manager (JRM) may be responsible for constructing entries in the JMS database 593 representing the jobs and services to be performed once a job request has been received. In step 714, job requests 613a may be deposited into an input folder 613 by the dump monitor, as described above in relation to FIG. 6. The job requests 613a may also be generated externally by more directly integrated systems, for example, for testing or where a higher degree of system integration exists. The input folder may be part of a file repository which is capable of generating an event notification signal to the JRM indicating that a new file has been received.

In step 715, the JRM may wait until it receives a notification that a new file has been stored in the input folder 613. Upon receipt of a notification signal, the JRM may determine whether the file is a job request. If the file is not a job request, the JRM may simply continue waiting for a job request.

In step 716, upon receipt of a job request 613a, the job request manager may verify that the job is correct. Job requests 613a may be stored in a particular format, for example, XML, or any other structured file containing job information. If job requests 613a are stored in XML format, the validation step 716 may use an XML document type definition (DTD) 724 to validate the structure of the job request. While XML is used for exemplary purposes in this description, it should be understood that any structured file containing the same information would also be acceptable. The JRM may further verify that the values in the job request 613a conform to predetermined values using client and license data 725 stored in the JMS database 593 as another validation step 716.

In step 717, the JRM may determine whether the job request is valid based on the verification performed in step 716. If the job request is not valid, the JRM may reject the job 718, and return to step 715 to wait until it receives notification of a new job request 613a. If the job request 613a is valid, the JRM may accept the job, and continue to step 720.

In step 720, the JRM may create service requests that prescribe what services are to be performed for the job. This step is detailed in FIG. 8. Once all of the service requests for the job have been created, the JRM may move all files, including the job request 613a from the input folder 613 to a repository 728. The JRM may then update a job request queue 726 and a service request queue 727 to indicate the status of the current job. The JRM may then return to step 715 to wait for more job requests.

Figure 8:
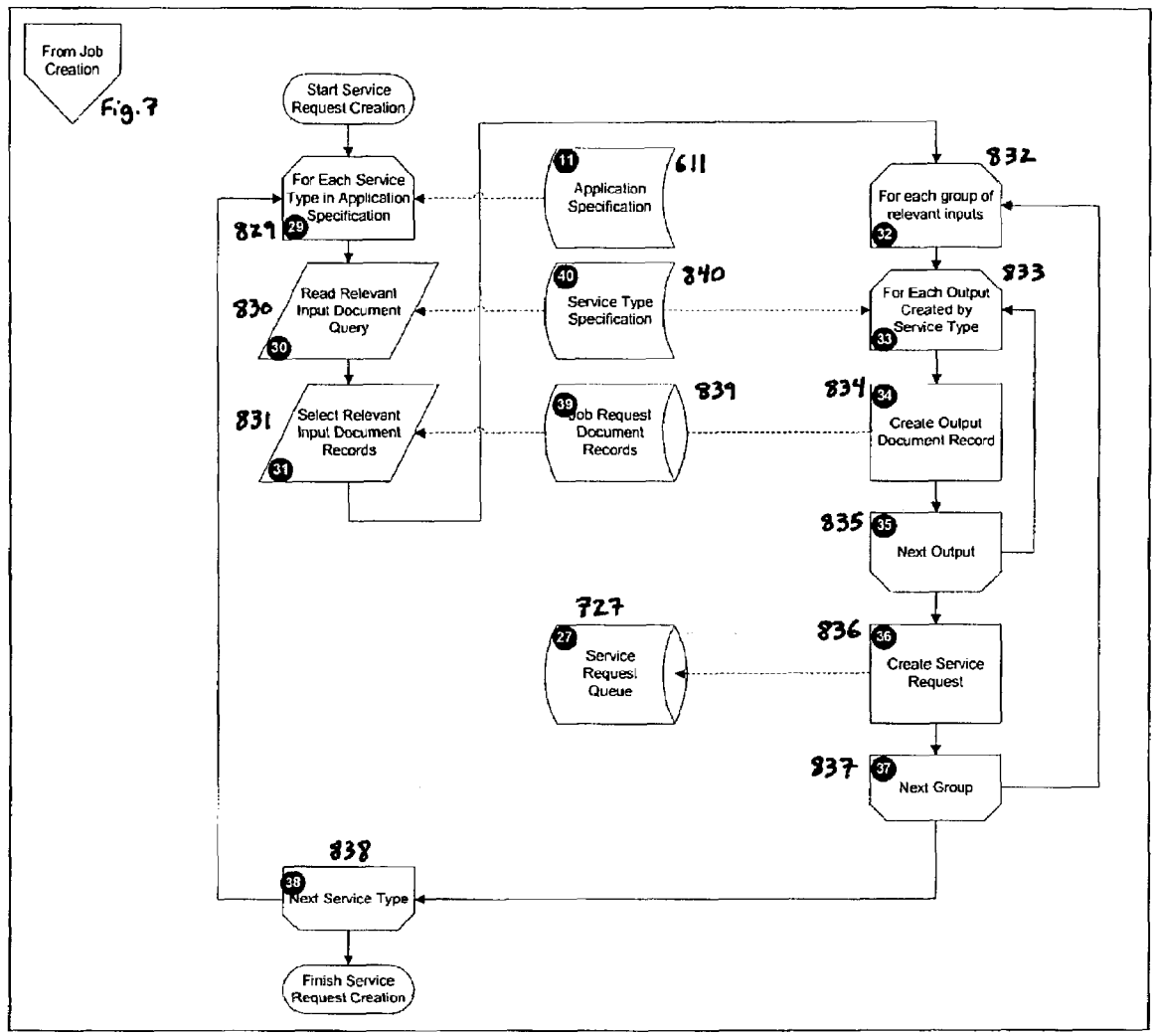
FIG. 8 is a flow diagram detailing service request creation steps according to one embodiment of the invention.

FIG. 8 expands on step 720, showing the details of the creation of service requests. One feature of the JMS is that it can support multiple applications, whereby each application is composed of a number of steps that may be performed on an input file or on the output of previous steps. This information may be recorded for each application supported by the JMS as an application specification 611 in its database. The JMS can then determine from the application specification what services must be used to complete the job. FIG. 8 details the steps followed by the JMS in making this determination.

In steps 829–838, the JRM may loop over each service type that must be performed on the job, as dictated by the information contained in the application specification 611. In step 830, the JRM may obtain a query from the service type specification 840 that indicates which documents for the job request are inputs to the service type. The query may also group the documents such that each group is related to a single service request. In step 831, the JRM may perform the query obtained in step 830 against a list of job request document records 839. The list of job request document records 839 may initially contain records only for those documents that were provided in the job request; however, as the process proceeds, the data store may gain new document records that may be used as inputs for subsequent steps.

In steps 832–837, the JRM may loop over each group of related inputs in the results obtained from step 831. In steps 833–835, the JRM may loop over each output created by each service type as specified by the service type specification 840. Thus, for each output created by each service type for each group of relevant inputs, the JRM may create an output document record 834, which may be stored in the job requests document records store 839. In step 836, a service record may be created in the service request queue 727. The service record may correspond to a unit of processing that may be performed on a data extraction server by some service process.

Figure 9:
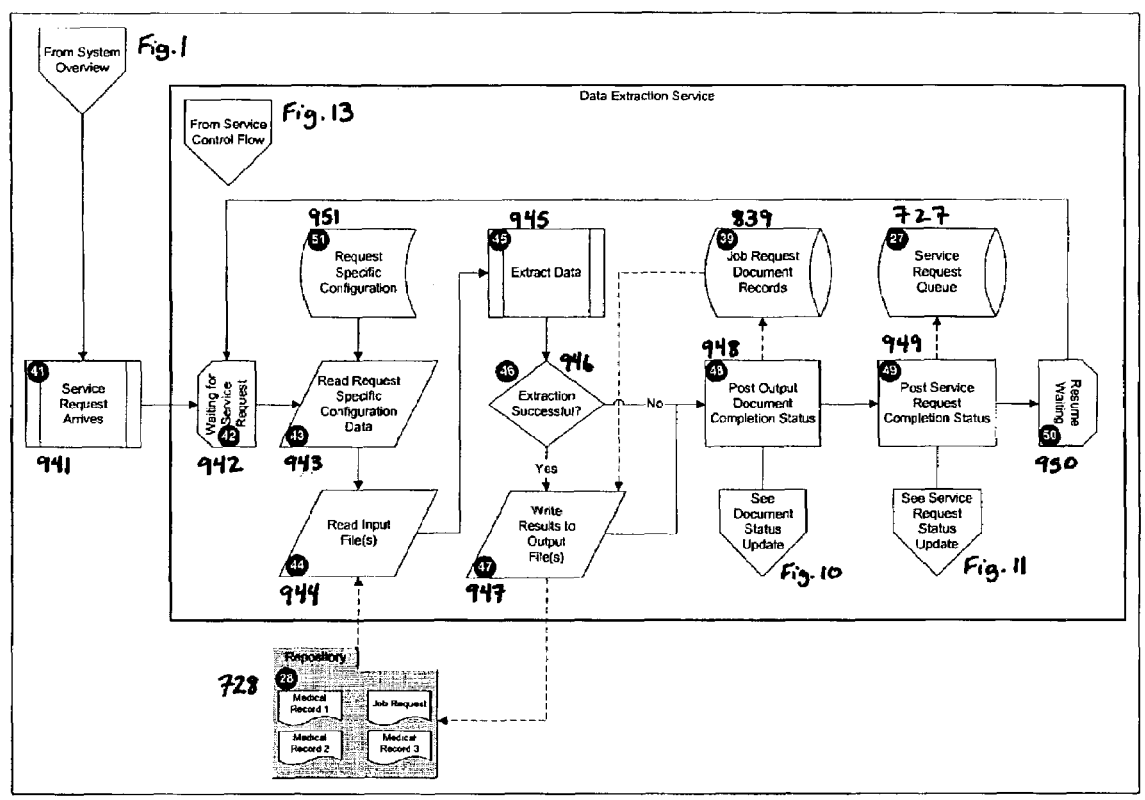
FIG. 9 is a flow diagram detailing data extraction steps according to one embodiment of the invention.
Figure 10:
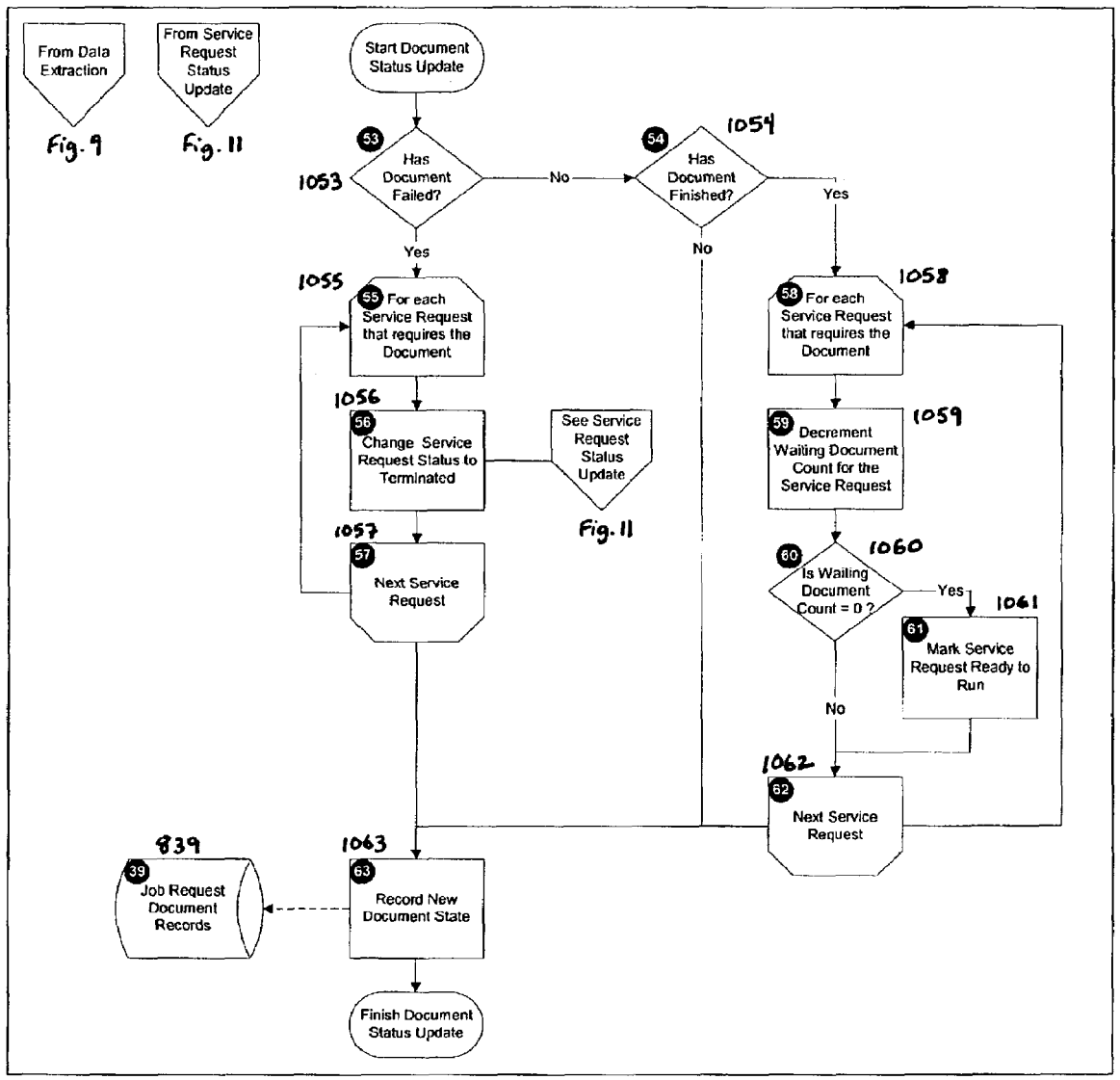
FIG. 10 is a flow diagram detailing document status update steps according to one embodiment of the invention.
Figure 11:
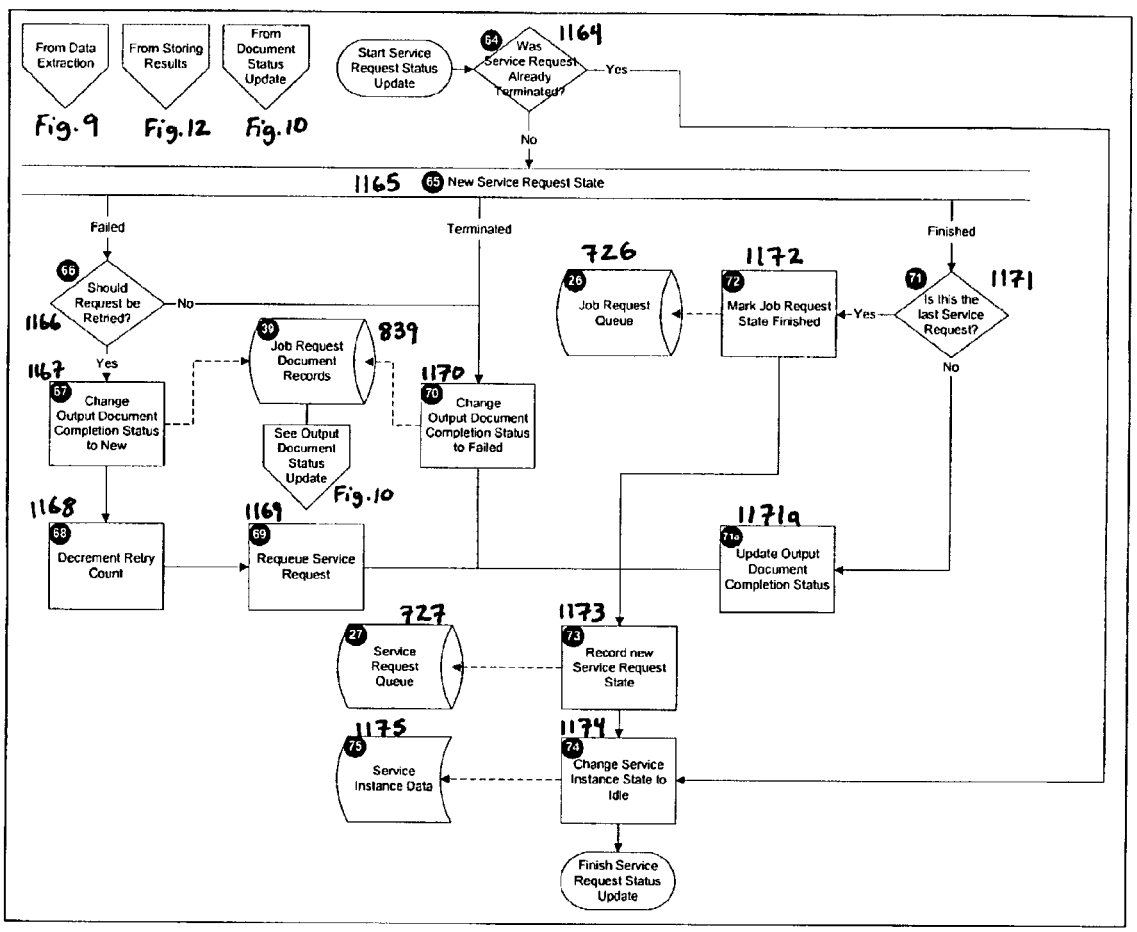
FIG. 11 is a flow diagram detailing service request status update steps according to one embodiment of the invention.

FIGS. 9–11 detail the steps performed for data extraction 503. In step 941, a service request may arrive. Service request arrival may occur when it becomes ready to run, which may be indicated when all of its required inputs are complete and all optional inputs are either complete or failed. A data extraction service may wait in a polling loop 942 for service requests, periodically asking the JMS database for a service request that is ready for processing.

Upon arrival of a service request 941, in step 943 the data extraction service may obtain any service request specific configuration parameters 951 from the JMS database 593. The specific configuration parameters 951 may be specified for service requests of a given type, for a specific instance of the data extraction service, for a given client or license used by the client, or for the application that the service request services, for example. These parameters may be used to control the type of processing performed in subsequent steps.

In step 944, the data extraction service may read input files from the repository 728. The data extraction service may optionally make local copies if needed or desired. In step 945, the data extraction service may extract information from the input files. Extractions may include, for example, simple reformatting (e.g., ASCII text to XML, or transformations of XML in one schema to another using XSL), aggregation of information from several inputs into one output, identification of specific features of interest in the inputs, performing FFTs (Fast Fourier Transforms) on audio or image data, converting images from one format to another (e.g., BMP to JPG), or any of a number of possible manipulations, transformations, or extractions that can be performed on any of a number of different file types.

Step 946 determines whether the extraction step 945 was successful. If the extraction step 945 was successful, the results from the extraction step 945 (i.e., the extracted data) may be written 947 to the repository 728 in locations which may be specified in the associated job request document records 839. If the extraction process was not successful, the results writing step 947 may be skipped.

In step 948, the status of each output document may be updated for each relevant job request document record 839 to reflect whether the job is complete, or whether the job must be retried. The document status update step 948 is detailed in FIG. 10.

In step 949, the data extraction service posts the state of the present service request as complete, failed, or failed unrecoverably. Service requests may fail, for example, due to intermittent errors in one or more of the hardware components comprising the system, or they may failed due to an unrecoverable error. If failure is due to hardware errors, the request may be completed successfully if tried again later. The service request status update step is detailed in FIG. 11.

In step 950, if the service request failed, the system may wait for a specified time period (e.g., one minute), then resume polling at step 942. If the service request was successful, the system may simply resume polling at step 942 without waiting. If the system waits for a specified time period, this may allow time for any transient conditions (e.g., network errors or other intermittent failures) that may have caused the failure to be corrected. If there are other data extraction services that can process the request and may not be suffering from the problem that caused the failure, then the delay may give them a chance to process the request before the failed extraction service tries again.

The document status update step 948 is detailed in FIG. 10. During document status updates, the JMS may determine whether downstream service requests are ready to run or whether they should be terminated because of a failure of a necessary upstream process. In step 1053, the system may determine whether a new document status is failed. If it is determined that the document status is not failed, then in step 1054, the system may determine whether the document status is finished. If it is determined that the not failed document is also finished, then the system may proceed to step 1058, described below.

If it is determined in step 1053 that the document status is failed, then the system may loop over all service requests that requires the failed document in steps 1055–1057. For each service request that requires the failed document, the service request status may be changed to terminated in step 1056 because the document cannot be used in the downstream requests. The service request status update step 1056 is detailed in FIG. 11. After the loop over service requests requiring the failed document in steps 1055–1057 is complete, the system may proceed to step 1063, described below.

In steps 1058–1062, the system may loop over all service requests that require the finished document. In step 1059, a counter associated with a service request that enumerates the number of documents required by that service request may be decremented to reflect the fact that one of the documents required by that service request is finished. In step 1060, the system may determine whether the waiting document count for that service request is zero, thus indicating that all of the documents required by that service request are finished. If so, the system may mark that service request ready to run in step 1061 and proceed to the next service request in the loop 1062. If not, the system may simply proceed to the next service request in the loop 1062. After all of the service requests requiring the finished document have been processed thus, the system may proceed to step 1063.

In step 1063, the status of the document as failed, not failed, but not finished, or finished may be recorded in the job request document record 839.

FIG. 11 details the service request status update step. When the service request status is updated, the JMS may allow failed requests to be re-queued with the hope that the cause of the failure is a transient error. Service request status updates also ensure that the document status may be correctly updated for failed or terminated service requests, so that requests further downstream may be appropriately terminated as well. Finally, if this is the last service request to finish, then the job may be marked as being finished in the job queue.

In step 1164, the system may determine whether the service request has already been terminated. If it has, the system may proceed to step 1174, explained below. If the service request had not been terminated, the system may determine what the new service request status is in step 1165. If the new service request state is failed, the system may proceed to step 1166. If the new service request state is terminated, the system may proceed to step 1170. If the new service request state is finished, the system may proceed to step 1171.

For failed service requests, the system may determine whether the failure is potentially recoverable in step 1166, and may determine whether the request should be retried based, for example, on a comparison of the number of previous attempts to a predetermined number of times that the request should be retried before it is deemed failed. If the request should not be retried, then the system may proceed to step 1170. If the request should be retried, the system may proceed to step 1167.

In step 1167, the output document completion status may be changed to new, and this status may be saved on the job request document record 839, as detailed in FIG. 10. In step 1168, a counter that tracks the number of times the request has been retried may be decremented. In step 1169, the service request may be re-queued by changing its state back to ready to run, and the system may proceed to step 1173.

In step 1170, the status of all output documents that have not already been marked as failed may be marked as failed to ensure that downstream requests waiting for the document do not start using a document produced by a failed service request. The system may then proceed to step 1173.

In step 1171, the system may determine whether the present service request is the last service request in the job. If so, then the system may proceed to step 1172. If not, the system may proceed to step 1171*a*, in which the status of the output document may be updated from its transitional to its final state: a document with a status of retry may be updated to failed, and a status of complete may be updated to finished. The purpose of the transitional states is to prevent downstream services from starting before the service request that produces a document has completed. If the document status was marked as finished directly by the service request in step 948 (detailed in FIG. 10), then downstream service requests could start work using that document. This would be undesirable because should the currently executing service fail and be retried, the input document for the downstream service requests may be recreated, possibly with different information.

In step 1172, the job request state may be marked as finished, and recorded in the job request queue 726.

In step 1173, the new service request state may be recorded in the service request queue 727. In step 1174, the service instance state may be changed from processing to idle in the service instant data record 1175.

Figure 12:
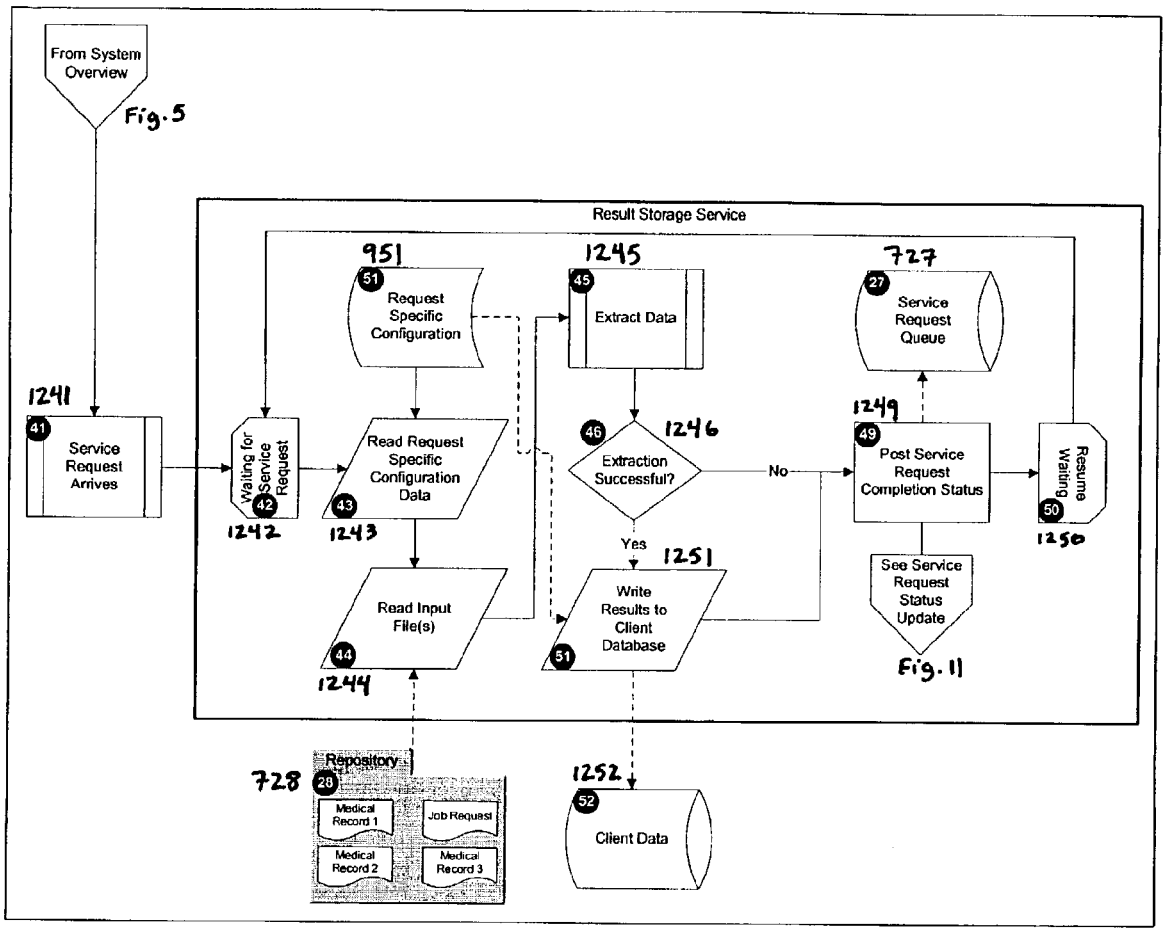
FIG. 12 is a flow diagram detailing steps for storing results according to one embodiment of the invention.

FIG. 12 details the step of storing results 504. Result storage services work similarly to data extraction services, except that the extracted results may be marshaled to systems external to the JMS. In step 1241, a service request may arrive when it has become ready to run, for example, when all of its required inputs are complete, and all optional inputs are either complete or have failed. A result storage service may wait in step 1242 in a polling loop for service requests to arrive 1241. The storage service may periodically query the JMS database 593 for a service request that is ready for processing.

Upon arrival of the service request 1241, the result storage service may obtain any service request specific configuration parameters 951 from the JMS database 593 in step 1243. These parameters may be specified for service requests of a given type, for a specific instance of the data extraction service, for a given client or license used by the client, for the application that the service request services, or they may specify any other suitable criteria. These parameters may be used to control the destination of the results or the type of processing that may be performed in the following steps.

In step 1244, the result storage service may then read input files from the repository 728, potentially making local copies if needed or desired. In step 1245, the result storage service may extract information from the input files. Extractions may include simple reformatting (for example, converting ASCII text into XML, or transforming XML in one schema to another using XSL), aggregation of information from several inputs into one output, identification of specific features of interest in the inputs, performing FFTs (Fast Fourier Transforms) on audio or image data, converting images from one format to another (e.g., BMP to JPG), or any of a number of possible manipulations, transformations, or extractions that can be performed on any of a number of different file types.

Step 1246 may determine whether the extraction step 1245 was successful. If the extraction step 1245 was successful, the results from the extraction step 1245 (i.e., the extracted data) may be written 1251 to the client database 1252. If the extraction process was not successful, the results writing step 1251 may be skipped.

In step 1249, the data extraction service may post the state of the service posts the state of the present service request as complete, failed, or failed irrecoverably. Service requests may fail, for example, due to intermittent errors in one or more of the hardware components comprising the system, or they may failed due to an unrecoverable error. If failure is due to hardware errors, the request may be completed successfully if tried again later. The service request status update step is detailed in FIG. 11.

In step 1250, if the service request failed, the system may wait for a specified time period (e.g., one minute), then resumes polling at step 1242. If the service request was successful, the system may simply resume polling at step 1242 without waiting. If the system waits for a specified time period, this may allow time for any transient conditions (e.g., network errors or other intermittent failures) that may have caused the failure to be corrected. If there are other data extraction services that can process the request and may not be suffering from the problem that caused the failure, then the delay may give them a chance to process the request before the failed extraction service tries again.

Figure 13:
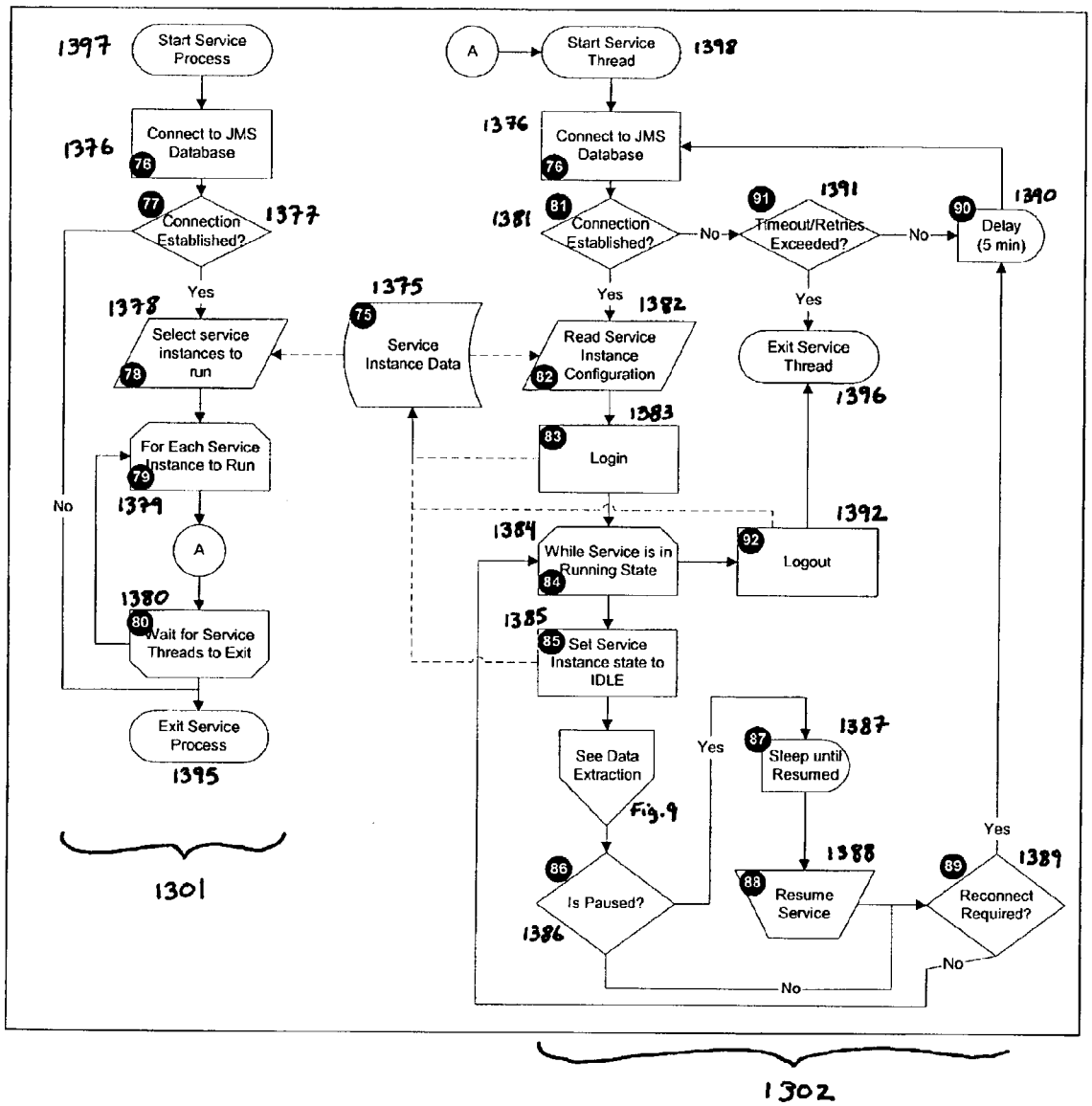
FIG. 13 is a flow diagram detailing steps for an application service control according to one embodiment of the invention.

FIG. 13 details the processes of service control flow that may be used as part of the service processes of the invention described above. Services may be daemon processes running on data extraction servers. FIG. 13 provides details about how these processes may be initialized and configured. While FIG. 13 shows control flow for a data extraction service, other services such as the JRM and dump monitor may use the same flow. These other services may be represented by exchanging the data extraction step referring to FIG. 9 with the document delivery step (FIG. 6), or job creation step (FIG. 7), for example. Services may be multithreaded processes, with threads for each service instance that the service process controls, and a main thread 1301 that may be used to manage service instance threads 1302 (e.g., to pause, resume, or stop the service instance threads).

When the service process main thread 1301 starts 1397, it may connect 1376 to the JMS database 593. In step 1376, the system may determine whether a connection has been established. If not, the service process may exit 1395. If a connection to the JMS database 593 has been established, the service process may select which service instances to run 1378 by querying the service instance data 1375 stored in the JMS database 593. This information may indicate, for example, which service types run on what computer systems. In steps 1379–1380, the system may loop through each service instance to run, creating and starting a new thread 1398 for each service instance to run. The loop may wait for service threads to exit 1396 and may handle any manually generated messages to each service instance, pausing, resuming, or stopping service threads as necessary. When all service threads have stopped, the service process may exit 1395.

Each service thread 1302 started 1398 by the main thread 1301 may open a connection 1376 to the JMS database 593. If a connection cannot be established, the process may continue at step 1391. If a connection to the JMS database 593 is established, the service instance may read instance specific configuration information 1382 from the service instance data 1375 from the JMS database 593 to configure the service instance.

In step 1383, the service instance may log into the JMS system, updating the service instance data 1375 to tell the system that it is available for processing. The service instance may then loop 1384 indefinitely, while it is in a running state. If no longer in a running state (e.g., it has been stopped by an operator), then the service instance may proceed to step 1392. Upon entry into the loop, the service instance may set its state in the service instance data 1375 to idle 1385, then call upon its main processing loop, whether it be the data extraction steps of FIG. 9, the document delivery steps of FIG. 6, the job creation steps of FIG. 7, or any other process.

Upon return from its main processing loop, the service instance may determine whether the main processing loop exited because a pause request was received 1386. If no pause has been received, the process may continue at step 1389. If a pause has been received, the process may sleep 1387 until it receives notification that it has been resumed. Once an operator has resumed the process 1388, the service processing may continue.

At step 1389, the service instance may verify whether it needs to reconnect to the JMS database 593. If not, then execution may continue at step 1384. If a reconnection is required, then processing may continue with step 1390. At step 1390, the service may enter a delay loop, sleeping for a predetermined time period (e.g., five minutes) before it then tries to connect again at step 1376. If a connection can still not be established, the system may determine 1391 whether the timeout or the number of retries, or some other indicator regarding connecting or reconnecting to the JMS database 593, have exceeded some predetermined value, then the service thread may exit 1396.

Upon a normal exit 1392, the service instance may log itself out of the JMS database 593, updating the service instance data 1375 in that database to record the fact that it is no longer available, and the thread may then exit.

FIGS. 14–30 detail a particular embodiment of the method of the invention involving the coding of inpatient medical records. In this embodiment, the systems and methods of the invention are used to assign ICD-9-CM and other codes to the medical records for hospital inpatients. The dashed lines represent data flow into and out of various databases, tables, or other information repositories. Solid lines represent the flow of control between the various steps in each process.

Figure 14:
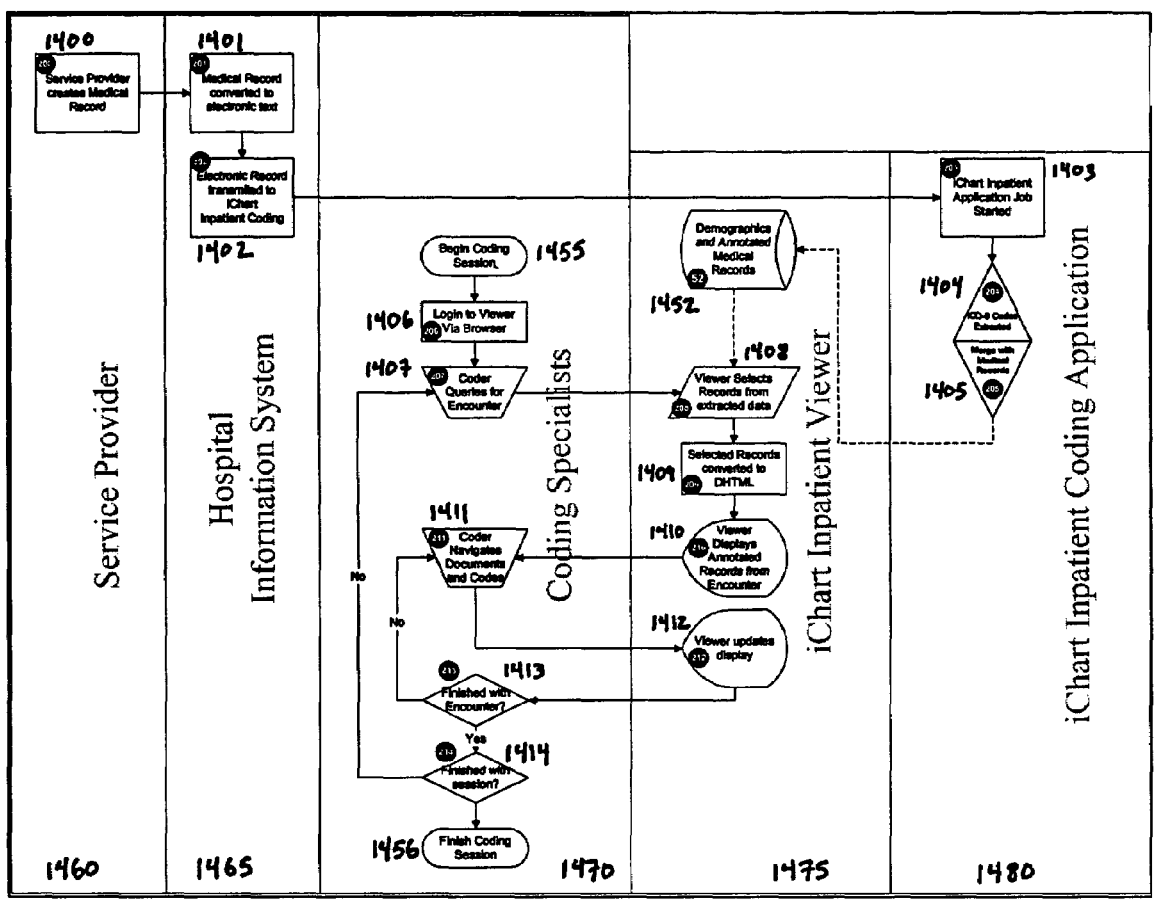
FIG. 14 is a flow diagram providing an overview of a method for inpatient information coding of medical records according to one embodiment of the invention.

FIG. 14 is a flow diagram providing an overview of the method. Medical service providers 1460, such as physicians and nurses, may create medical records of encounters with patients using their normal procedures in step 1400. The medical records may be converted to electronic format if necessary in step 1401 on a hospital side information system server 1465. The conversion to electronic format may be through transcription from a voice file, by direct entry into the computer system, or through computer assisted transcription of a voice file, for example.

The electronic record may be transferred in step 1402 to the coding application 1480. The coding application may create a new job to extract codes, as detailed above in FIGS. 6 and 7. ICD-9-CM codes may be identified for the input records in step 1404 as described in further detail below. In step 1405, the extracted codes may be merged with any demographic data in the records, and stored in the client database 1452. This step is also described in further detail below.

Coding sessions 1455 involve coding specialists 1470 reviewing and refining the results of the coding application. In step 1406, coding specialists may log in to a website using a viewing application running in a web browser. The coding specialists may enter a query in step 1407 to select a medical record of an encounter. In step 1408, the viewer application 1475 may translate the coding specialists' selection into a database query and select the appropriate records from the client database 1452. The selected records may then be converted 1409 to dynamic hypertext markup language (DHTML), which can be displayed 1410 by; the coding specialists' web browser.

Coding specialists can then navigate through the medical records, reviewing the codes supported by the record, or can navigate through the codes, reviewing the text supporting each code. In response to the coding specialists' commands, the viewing application may update the information displayed on the browser in step 1412. As long as the coding specialists continue to navigate through the record, the process cycles between steps 1411 and 1412. When the coding specialists finish with the encounter 1413, they may indicate a desire to review other records, thus returning to step 1407, or they may indicate that they are finished reviewing records, in which case the coding session is finished 1456.

Figure 15:
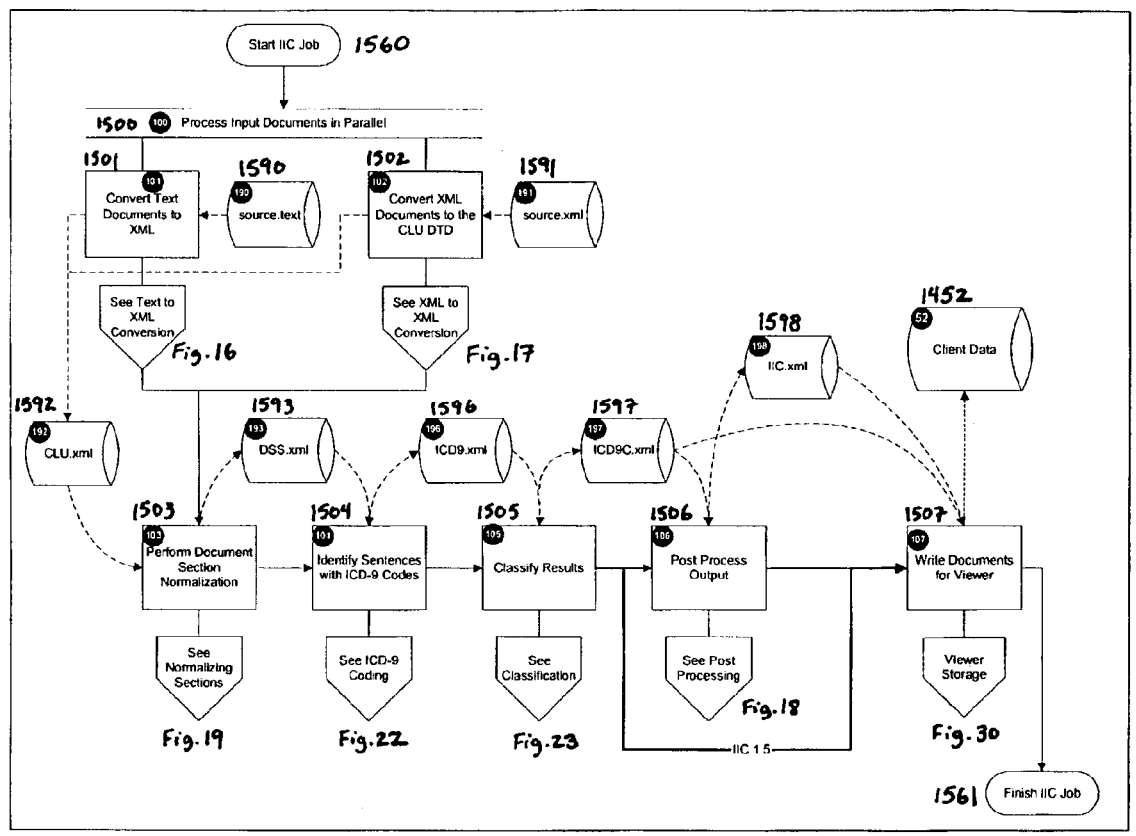
FIG. 15 provides an overview of steps in processing inpatient medical records according to one embodiment of the invention.

FIG. 15 provides an overview of the main steps in processing inpatient medical records. An inpatient information coding (IIC) job may be provided to the system in electronic format 1560. In general, there are two parallel routes 1500 through which IIC input jobs may be processed. If IIC jobs provide input source files in text format 1590, they may be converted to a conforming XML format in step 1501. This text to XML conversion is detailed in FIG. 16. The conforming format is defined as clinical language understanding document type definition (CLU DTD). A conforming format is preferred in order to allow the subsequent processing to be performed on a uniform document type. If IIC jobs provide input source files in XML format 1591, they may be converted to the conforming CLU DTD format in step 1502. This XML to XML conversion step is detailed in FIG. 17.

After the conversion step, CLU formatted documents 1592 may be normalized in step 1503, producing documents that are sectioned, with each section heading identified and normalized to produce a DSS (document segmentation service) document 1593. This normalization step is detailed in FIG. 19.

The DSS document may be subjected to a coding step 1504, which may identify text supporting ICD-9-CM or other relevant codes found in the input document 1593, and which may produce output that annotates the codes, thus producing an ICD9 document 1596. The coding step 1504 is detailed in FIG. 22.

The ICD9 document 1596 may be subjected to a classification step 1505, which may improve upon the results produced in the coding step 1504 by weighting and/or correcting the codes found in the input document 1596, thus producing a corrected output document, ICD9C 1597. The classification step 1505 is detailed in FIG. 23. The ICD9C document 1597 may be subjected to a post-processing step 1506, which transforms the document into an IIC document 1598, capable of being read by the viewer application. The post-processing step is detailed in FIG. 18. Note, however, that this post-processing step is preferably omitted, and instead the viewer application is preferably configured to be capable of viewing the ICD9C 1597 documents directly.

Finally, the ICD9C 1597 (and/or IIC 1598) document may be written 1507 to an output database 1452, which may be accessible by the viewer application. This step is detailed in FIG. 30. Writing 1507 the document to the database 1452 marks the end of the IIC job 1561.

Figure 16:
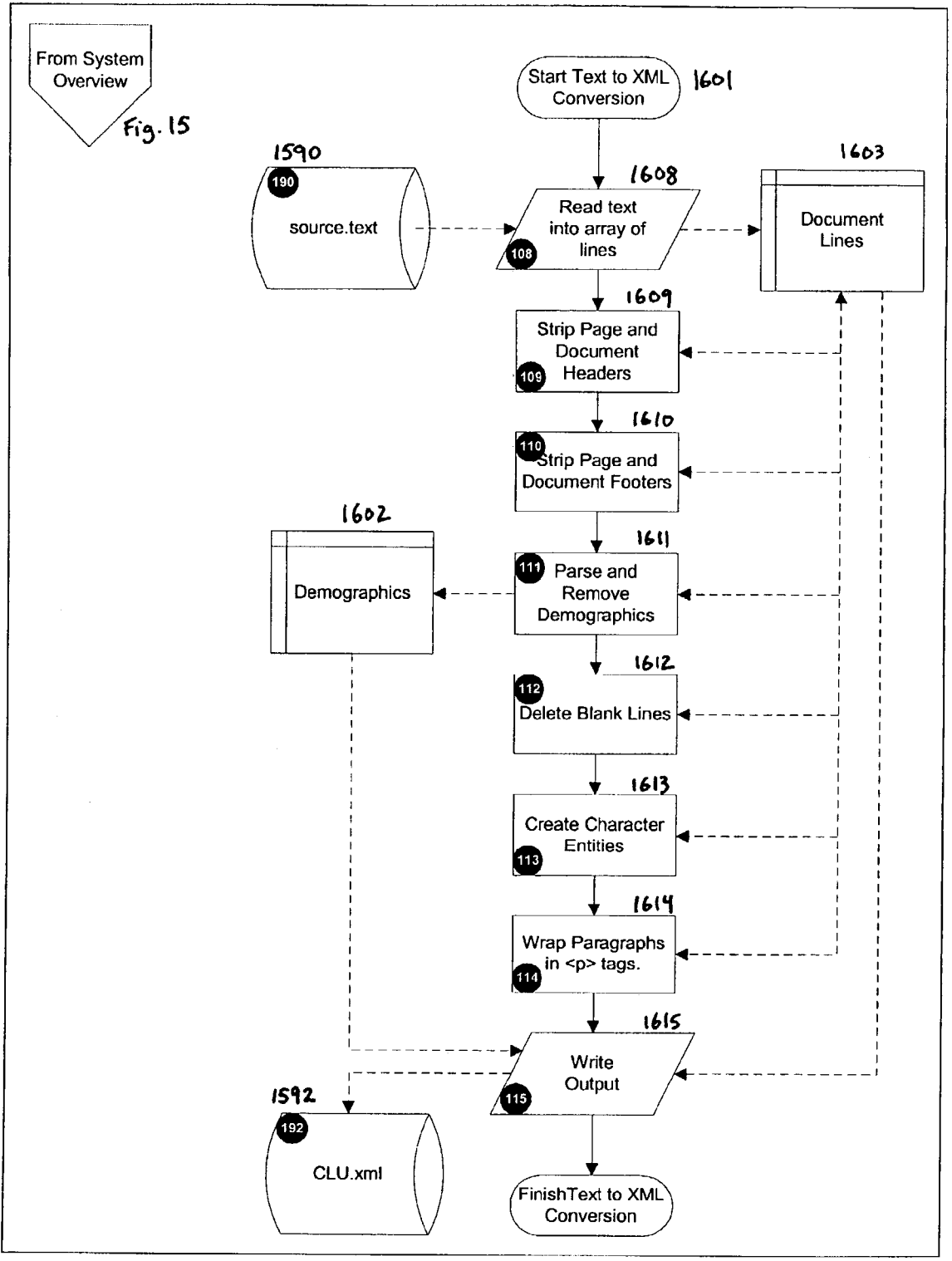
FIG. 16 is a flow diagram showing steps in a text to XML conversion process according to one embodiment of the invention.

FIG. 16 is a flow diagram showing the steps in the text to XML conversion process 1501. A source document in text format 1590 may be provided for text to XML conversion 1601. The text may be read from the source document 1590 into an array of lines 1603 in step 1608. Page and document headers may be identified in step 1609 using known patterns based on sample documents provided by the client, and may be stripped from the array of lines 1603. Page and document footers may be identified in step 1610 in a similar manner to step 1609, and may likewise be stripped from the array 1603.

Demographic data may be identified in step 1611 using known patterns based on sample documents provided by the client. This information may be recorded in memory in a demographics array 1602, and the demographic lines which are not part of the document content may be removed. In step 1612, blank lines may be deleted from the array of lines 1603.

Characters that do not fit into the printable ASCII range (i.e., hexadecimal values 20 to 7E) may be translated into characters that are predefined in the CLU XML format in step 1613.

Paragraph tags may be wrapped around the text in the array of lines 1603 in step 1614. There are several different ways to identify paragraphs depending on the format of the input supplied by the client. The simplest method is to wrap each line as a paragraph, but there are also more complex methods using white space and text cues to identify paragraph divisions.

Finally, the output file 1592 may be created in step 1615 by combining the remaining modified lines in the array with demographic data 1602 recorded in memory. The output file 1592 may be written in CLU XML format.

Figure 17:
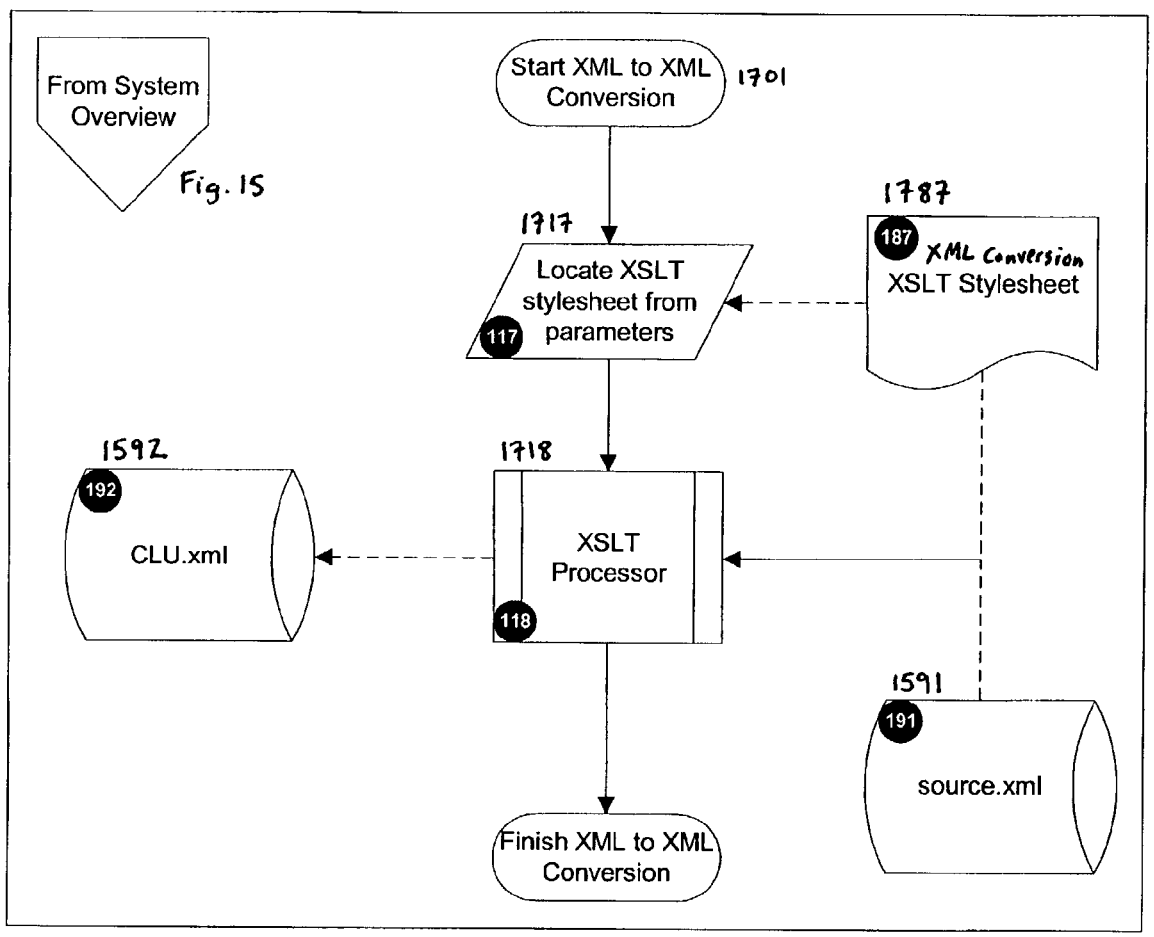
FIG. 17 is a flow diagram showing steps in a XML to XML conversion process according to one embodiment of the invention.

FIG. 17 is a flow diagram showing the steps in the XML to XML conversion process 1502. The process may begin 1701 when a source document in XML format 1591 is provided for the XML to XML conversion. An Extensible Style sheet Language Transformation (XSLT) style sheet 1787 used to perform the conversion may be located in step 1717 using request specific parameters passed to the converter. See James Clark, *XSL Transformations* 1.0, W3C, (Nov. 16, 1999), incorporated herein by reference. An XSLT processor 1718 may be passed to the style sheet 1787 and source document 1591. The output document 1592, conforming to the CLU DTD format, may then be saved.

Figure 18:
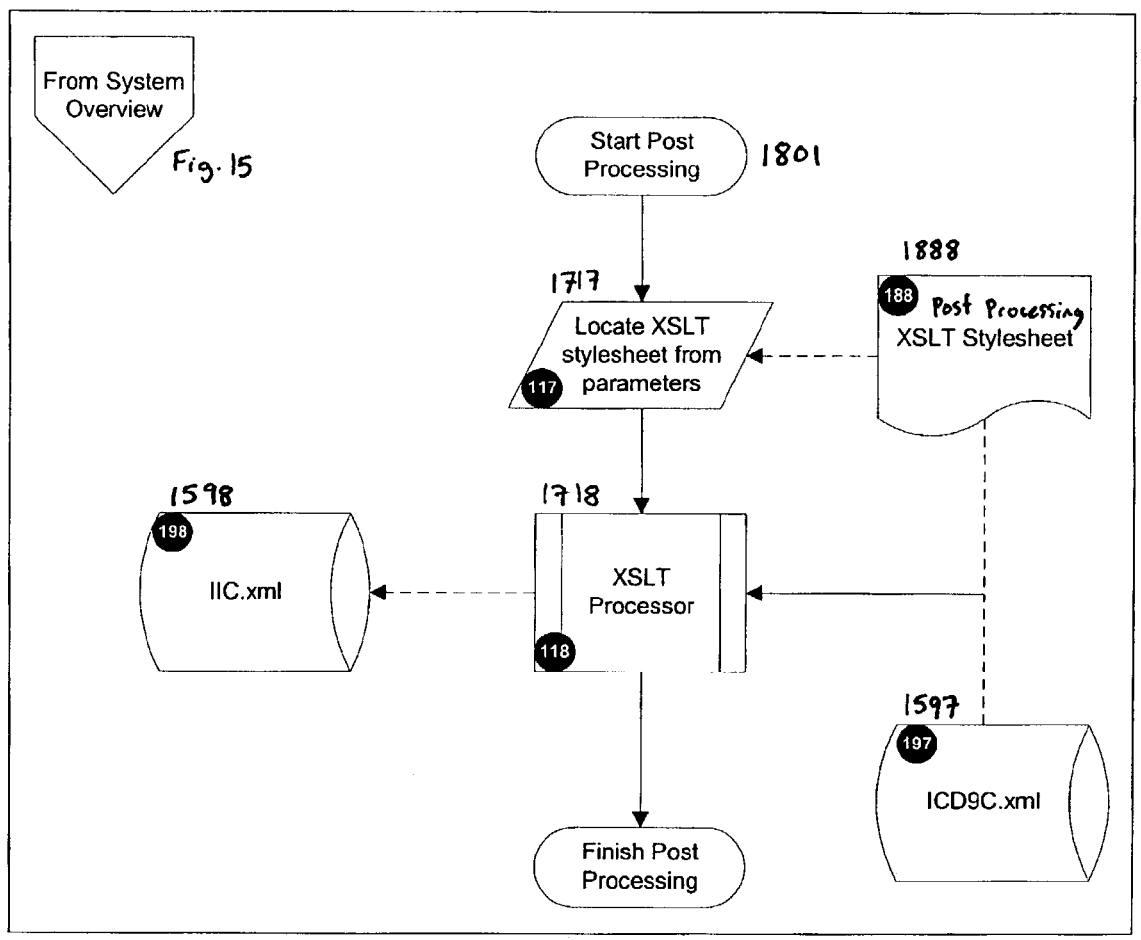
FIG. 18 is a flow diagram showing post processing steps according to one embodiment of the invention.

FIG. 18 is a flow diagram showing the post processing steps 1506 (if needed). It may be noted that the control flow for post processing is the same as the control flow for XML to XML conversion, namely, the simple application of an XSLT style sheet to an XML document to produce another XML document. The process may begin 1801 when the ICD9C document in XML format 1597 is provided. An XSLT style sheet 1888 used to perform the post processing may be located in step 1717 using request specific parameters passed to the converter. An XSLT processor 1718 may be passed the stype sheet 1888 and ICD9C document 1597. The output IIC document 1598 may be saved.

Figure 19:
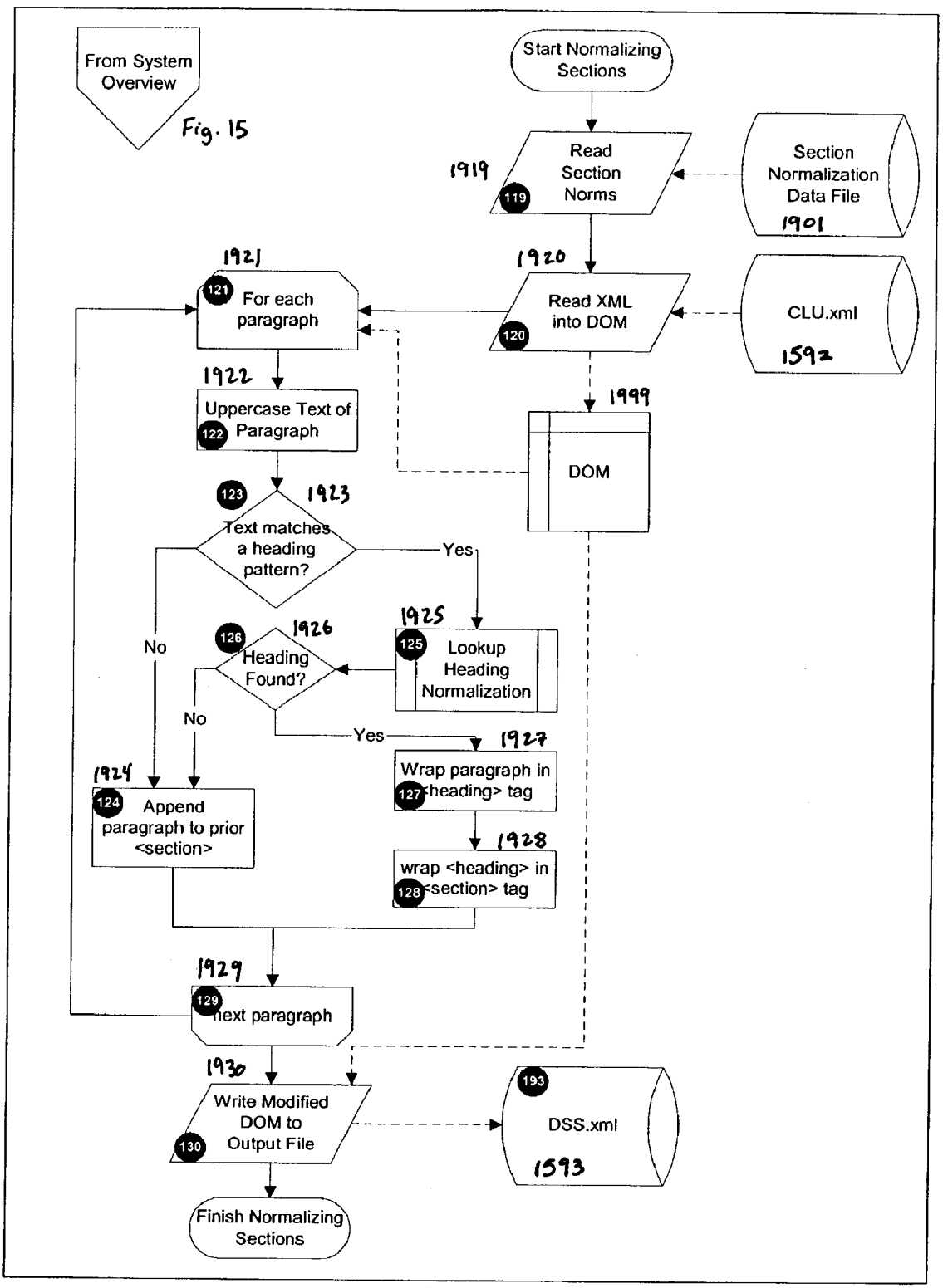
FIG. 19 is a flow diagram detailing normalization steps according to one embodiment of the invention.

FIG. 19 is a flow diagram detailing the normalization steps 1503. Section normalization converts paragraphs that were marked up in previous steps as section headings into section headings, and inserts paragraphs that were not marked up in previous steps as section headings into the identified sections. In step 1919, section norms may be read from a section normalization data file 1901 into memory. In step 1920, the input document 1592 may be read into memory as a document object model (DOM) 1999. For details about document object models, see Arnaud Le Hors et al., *Document Object Model (DOM) Level 2 Core Specification*, W3C (Nov. 13, 2000), incorporated herein by reference.

In steps 1921–1929, a loop over each paragraph in the document is performed. For each paragraph tag in the document 1921, the text content of the tag may be converted to uppercase in step 1922. The system may then determine in step 1923 whether the uppercase text content of the instant paragraph tag matches any of the heading identification patterns. If so, the system may proceeds to step 1925. If not, the system may proceed to 1924, and the instant paragraph may be appended to the prior section tag, if it exists. The system may then proceed to step 1929, and the loop continues 1921 or ends, thus permitting the system to proceed to step 1930.

Figure 20:
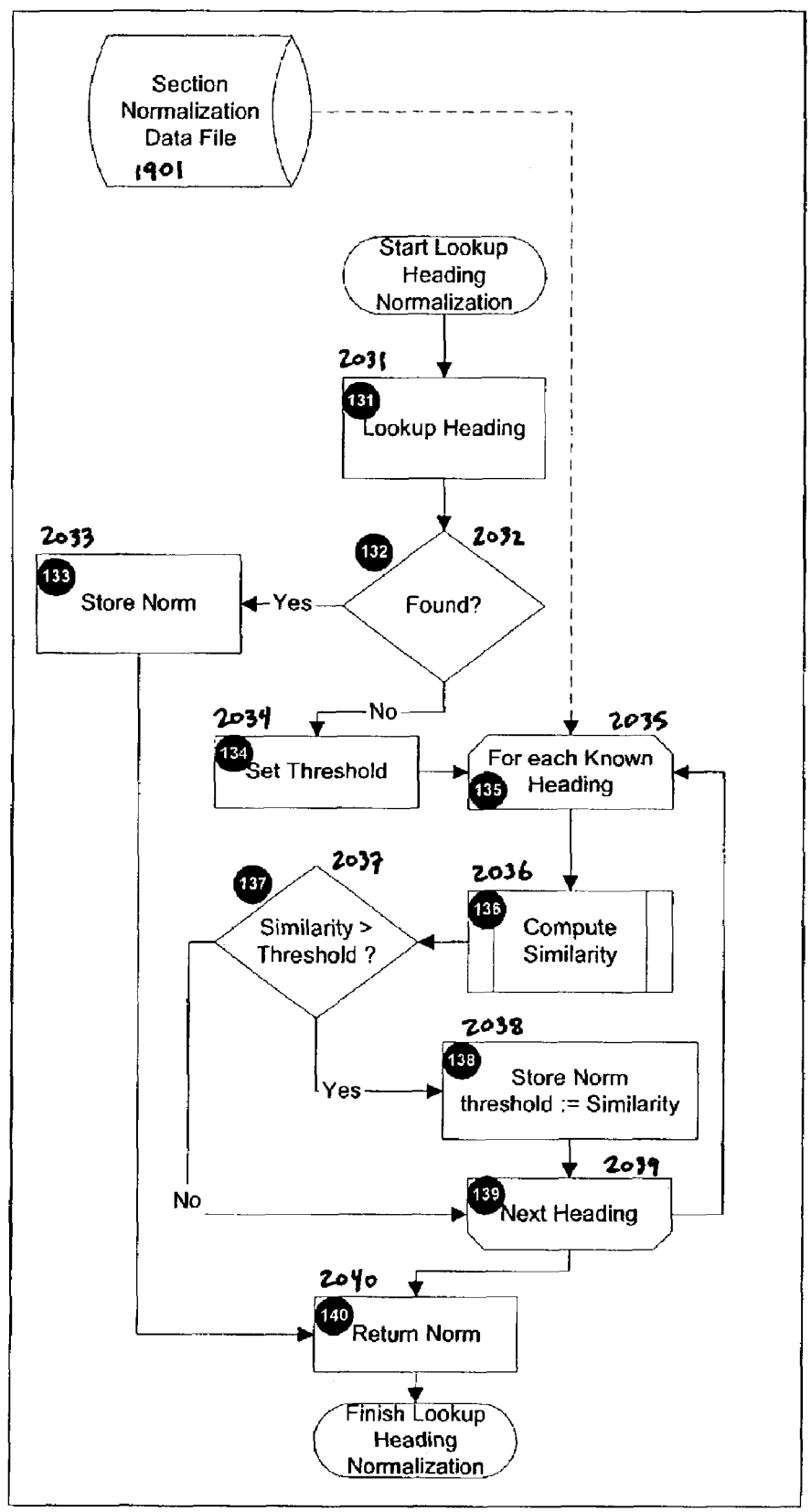
FIG. 20 is a flow diagram detailing steps involved in looking up normalizing headings according to one embodiment of the invention.

In step 1925, the system looks up the normalization for the heading as detailed in FIG. 20. The system then determines in step 1926 whether a heading was found. If so, then the system proceeds to step 1927. If not, the system may proceed to 1924, and the instant paragraph may be appended to the prior section tag, if it exists. The system may then proceed to step 1929, and the loop continues 1921 or ends, thus permitting the system to proceed to step 1930.

In step 1927, the contents of the instant paragraph tag may be wrapped in the heading tag found in the preceding steps. Then in step 1928, the heading tag found in the preceding steps may be wrapped in a section tag. The system may then proceed to step 1929, and the loop continues 1921 or ends, thus permitting the system to proceed to step 1930.

In step 1930, the DOM 1999 thus modified by the action of the loop described as steps 1921–1929 is written to the DSS output file 1593.

FIG. 20 details the steps involved in looking up normalizing headings. In step 2031, a heading candidate may be looked up in the section normalization data file 1901. Step 2032, may determine whether the candidate was found or not. If the heading candidate was found in step 2032, the norm associated with the heading may be stored in step 2033, and the heading norm that was found may be returned in step 2040.

If the heading candidate was not found in step 2032, then a predetermined similarity threshold may be set 2034 to a value sufficient to eliminate matches that are less than ideal. The similarity threshold may be determined empirically.

Figure 21:
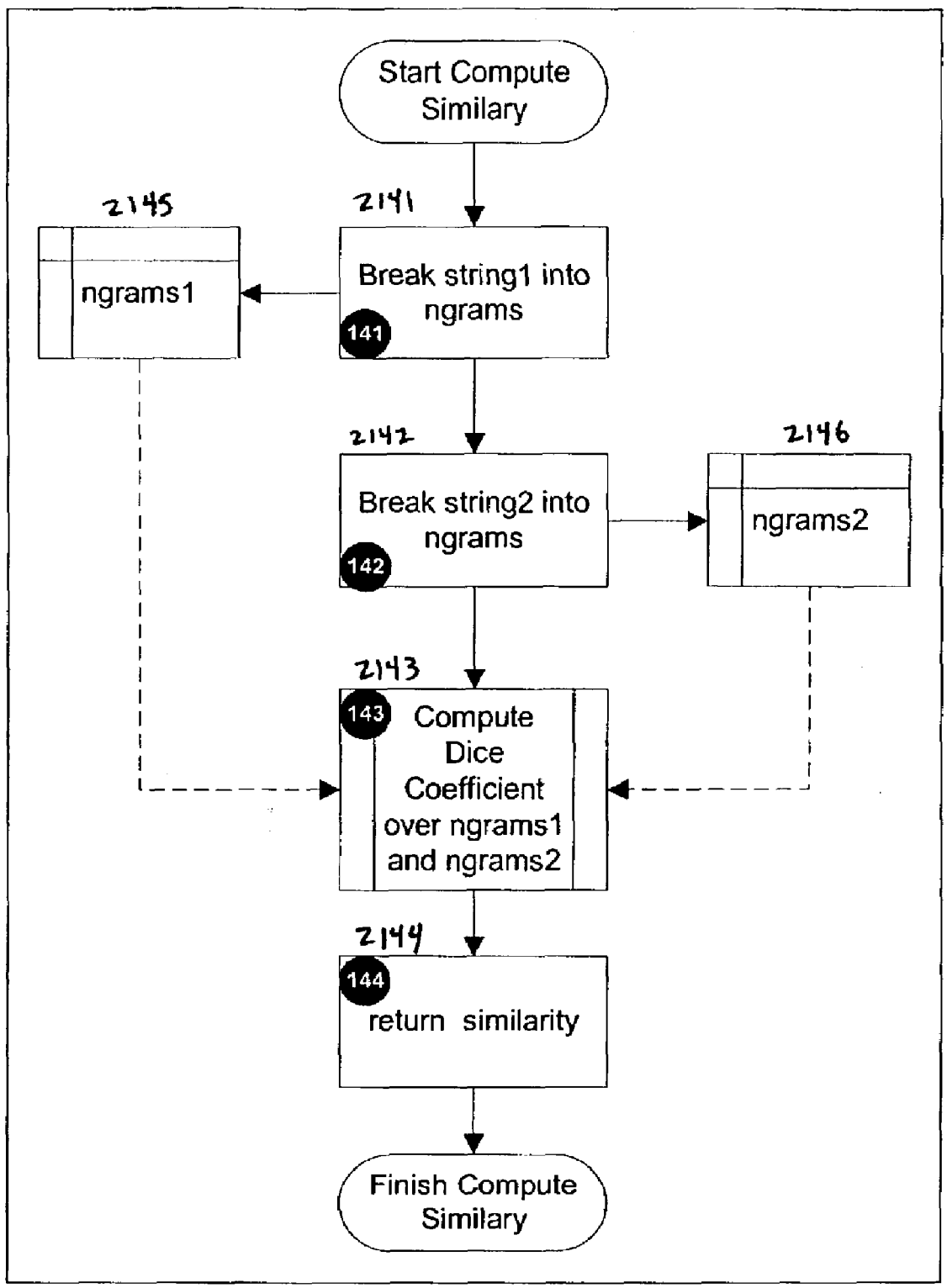
FIG. 21 is a flow diagram detailing steps involved in computing the similarity between known headings and candidate headings according to one embodiment of the invention.

A loop over each known heading may be performed in steps 2035–2039. For each known heading 2035, the heading's similarity to the candidate heading may be computed in step 2036. Step 2037 may compare the heading's similarity to the candidate heading to determine whether the similarity exceeds the predetermined similarity threshold set in step 2034. FIG. 21 details the steps involved in computing the similarity 2036. If the similarity is less than or equal to the threshold value, the loop continues 2039. However, if the similarity is greater than the threshold value, then the norm associated with the heading may be stored in step 2038, the threshold value is set to the value of the similarity computed in step 2036, and the loop continues with step 2039. In this way, the heading norm that is most similar to the candidate is selected and returned as the norm in step 2040.

FIG. 21 details the steps involved in one method of computing the similarity between known headings and candidate headings. This method involves the use of Dice's coefficients of similarity on sets of quadgrams produced over the known heading and the candidate heading. The use of Dice's coefficients is detailed in Lee R. Dice, *Measures of the Amount of Ecologic Associations Between Species*, J. Ecology 46 (1945), incorporated herein by reference. Dice's coefficient is a scalar set overlap function computed over two sets, A and B, as:

$$\mathrm{Dice}(A, B) = 2 \times \frac{|A \cap B|}{|A| + |B|}$$

In step 2141, the first string, corresponding to the candidate heading, may be broken into n-grams, including whitespace, of a preset size. In an alternative embodiment, the first string may correspond to the known heading, and the second string may correspond to the candidate heading. However, for the remainder of the description of this embodiment, the first string is assumed to be the candidate heading and the second string the known heading. In a preferred embodiment, the first string is broken into 4-grams in step 2141. The n-gram corresponding to the first string may stored in a first n-gram array 2145.

In step 2142, the second string, corresponding to the known heading, is broken into n-grams, including whitespace, of a preset size. Preferably, the first string is broken into 4-grams in step 2142. The n-gram corresponding to the second string may be stored in a second n-gram array 2146. In step 2143, the Dice coefficient is computed over the two sets of n-grams. In step 2144, the Dice coefficient is returned as the similarity.

Figure 22:
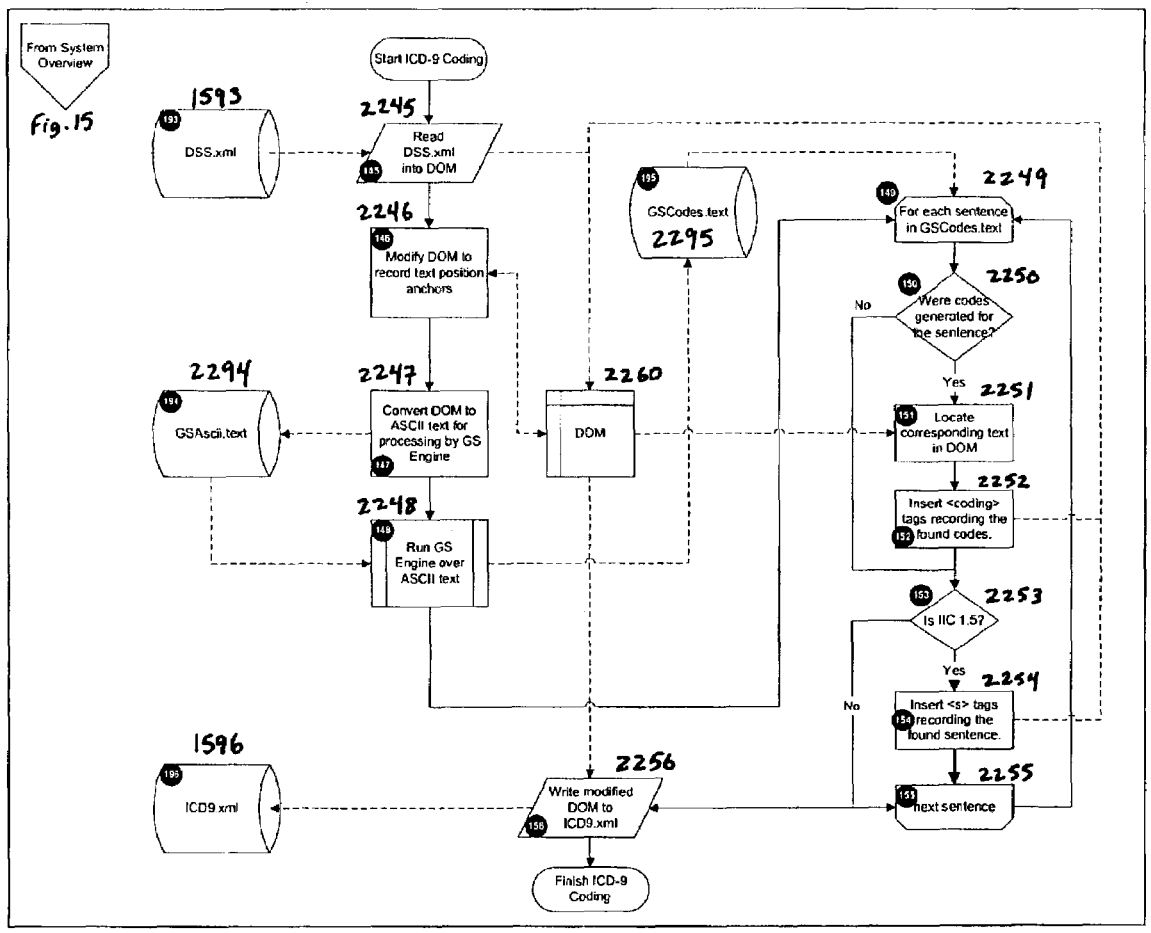
FIG. 22 is a flow diagram detailing generation of medical codes may be generated from text according to one embodiment of the invention.

FIG. 22 details how ICD-9-CM codes may be generated from the sectioned text. It should be understood, however, that while the steps described below use ICD-9-CM codes as an example, the method is easily generalized to any type of code known to those in the medical coding art including, but not limited to, CPT, SNOMED, or ICD-10, for example.

In step 2245, the input DSS document 1593 may be read into memory as a DOM 2260. In step 2246, the DOM may be modified to record the position of text in the tree to generate a map of text position anchors. This step may wrap all text children of the DOM in new elements that record the starting and ending character positions of the wrapped text nodes. In step 2247, the DOM may be converted to ASCII text and written as in intermediate text file 2294.

The intermediate file may then be processed in step 2248 by a coding engine to produce a corresponding codes text file 2295 that may contain the sentences that the engine identified, as well as the codes that are believed to be associated with the sentences. In one embodiment, the coding engine may be a Gabrieli-Speth (GS) engine. In another embodiment, any suitable coding engine may be used. In a preferred embodiment, the improved coding engine described herein may be used.

In steps 2249–2255, a loop over each sentence in the codes text file 2295 is performed. Step 2250 determines whether one or more codes were generated for the sentence. If not, then the system skips to step 2253. If so, then in step 2251, the system may locate the text corresponding to the one or more codes in the DOM 2260 using the map generated in step 2246. In step 2252, coding tags may be inserted as appropriate to record the codes found.

Step 2253 determines whether the file will require post-processing, or whether the system is the improved (IIC1.5) system. If the file will require post-processing, the loop may continue at step 2255, or if each sentence has been looped over, then the system may proceed to step 2256. If the file will not require post-processing because the system is the improved (IIC.1.5) system, then sentence tags may be inserted around the sentence that was identified in step 2254. The loop continues at step 2255.

When each sentence in the codes text file has been looped over, the text position elements added in step 2246 are removed, and the modified DOM file is written in step 2256, thus creating the ICD9 output file 1596.

Figure 23:
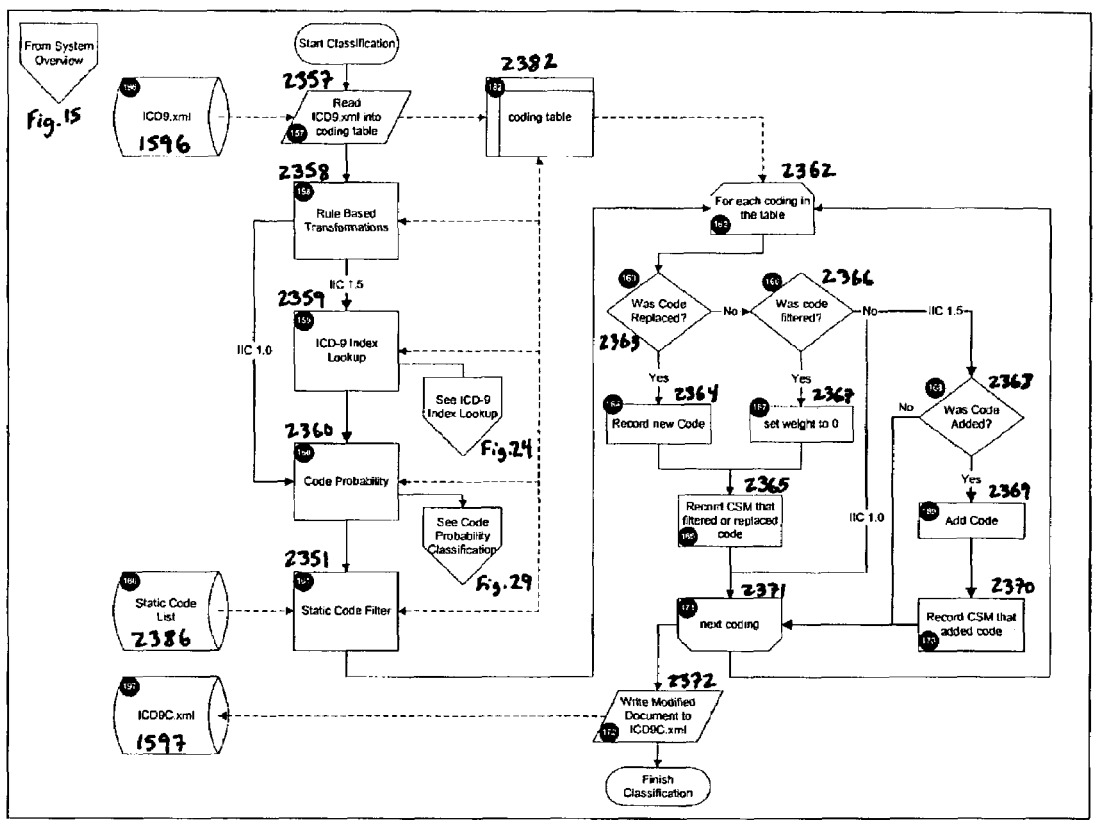
FIG. 23 is a flow diagram detailing steps involved in classifying codes according to one embodiment of the invention.

FIG. 23 details the steps involved in classifying codes. After the coding engine has produced coding results, they may be corrected and classified according to the likelihood that they would be useful to a coding specialist. In step 2357, the input file 1596 may be read into memory and converted into a coding table 2382 containing one entry for each coding tag found in the input. Preferably, if the system is a IIC1.5 system, this table also contains entries for each un-coded sentence tag.

In step 2358, a set of rule-based corrections may be performed. These corrections may use pattern matching to identify codes in the index, and the replacements that should be applied. The correction patterns may be produced by comparing the output of the coding performed by the coding engine by codes generated by human coders on the same encounters. Preferably, if the system is a IIC1.5 system, the next step is 2359. Otherwise, the system proceeds to step 2360.

In step 2359, additional codes may be produced by looking up phrases for coded and uncoded sentences in an index of phrases. This step is detailed in FIG. 24.

In step 2360, codes may be filtered based on the prior probability of correctness based on the success of previous coding attempts by the coding engine or ICD-9 (or other codes) index lookup modules. This step is detailed in FIG. 29.

In step 2361, codes may be further filtered by eliminating all codes that appear in a static list of codes to be removed 2386, for example, by setting the weight of these codes to zero. This step allows certain codes (e.g., signs, symptoms, ill-defined conditions, and certain ICD-9-CM codes with a V or E prefix) to be eliminated from the output before being displayed to the coder. These codes are often not relevant to coding encounters for billing. The static list of codes to eliminate may be customized for each client or for each job-type.

In steps 2362–2371, the classifier loops through each coding entry found in the coding table 2382. Step 2363 may determine whether a code was replaced. If not, the classifier may continue at step 2366. If a code was replaced, then the new code may be recorded in step 2364. In step 2365, the module that filtered or replaced the code may be recorded, and the loop through each coding entry may continue in step 2371. If each code in the table has been looped over, the classifier may proceed to step 2372.

If a code was not replaced, as determined in step 2363, the classifier determines in step 2366 whether the code was filtered. If not, then the classifier may proceed to step 2371. Preferably, however, if the system is the IIC1.5 system, the classifier may proceed to step 2386. If the code was filtered, as determined in step 2366, then the weight for the code may be set to zero.

Step 2368 determines whether a code was added for the sentence. If not, the classifier proceeds to step 2371, where the loop through each coding entry may continue. If a code was added for the sentence, then the code may be added to the coding table 2382 in step 2369. In step 2370, the module that added the code may be recorded.

After each code in the table has been looped over 2371, the classifier may proceed to step 2372, which writes the modified document to the output file 1597.

Figure 24:
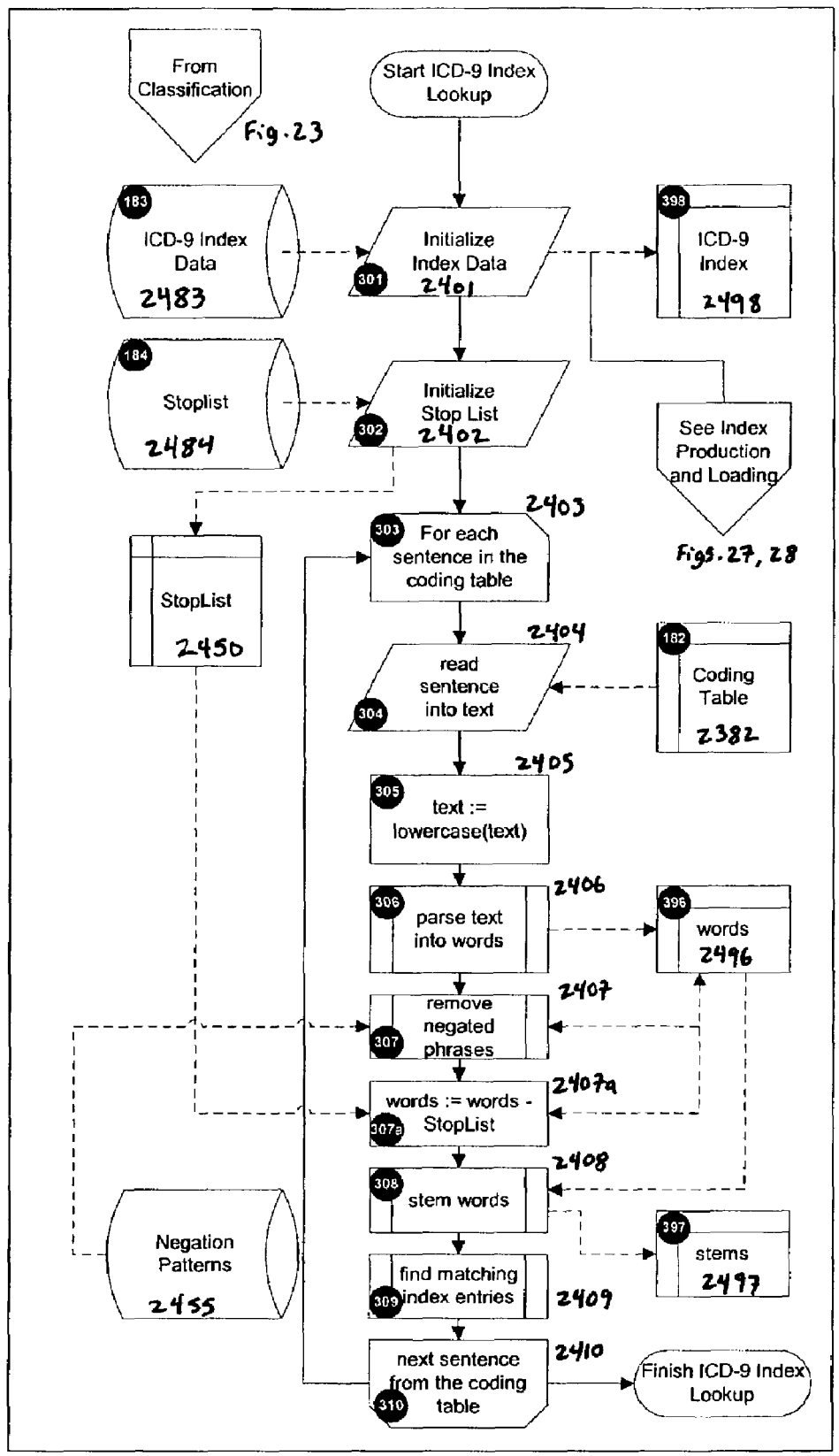
FIG. 24 is a flow diagram detailing steps involved in a coding index lookup according to one embodiment of the invention.

FIG. 24 details the steps involved in the ICD-9 index lookup step in the code classifying process. In step 2401, the ICD-9 index data file 2483 may be loaded into memory, and an ICD-9 index array 2498 may be produced. It should be noted that while the embodiment described here uses ICD-9 codes, it is a simple matter to generalize this process using any codes. The index production and loading steps are detailed in FIGS. 27 and 28.

The stop list 2484 may be loaded into memory in step 2402, and a stop list table 2450 may be produced. The stop list may contain a list of words that are considered not relevant when looking up phrases in the index.

Steps 2403–2410 loop over each sentence in the coding table 2382. In step 2404, the instant sentence text may be read into a local variable. In step 2405, the text may be converted to lowercase. In step 2406, the text may be broken into words at white space and punctuation boundaries, and the words may then be stored in a word array 2496. In step 2407, negated phrases may be identified using patterns from the negation patterns data file 2455. These may then be removed from the list of words 2496 produced in step 2406. In step 2407*a*, words appearing in both the list of words and the stop list may be removed from the list of words 2496.

In step 2408, each word in the list may be stemmed using an algorithmic stemmer, such as that described by Martin F. Porter, *An Algorithm for Suffix Stripping*, Program 14, 130–37 (July 1980), incorporated herein by reference. The results of stemming may be saved in a stems array 2497. In step 2409, matching index entries are found, as detailed in FIG. 25. The loop over the sentences in the coding table continues in step 310.

Figure 25:
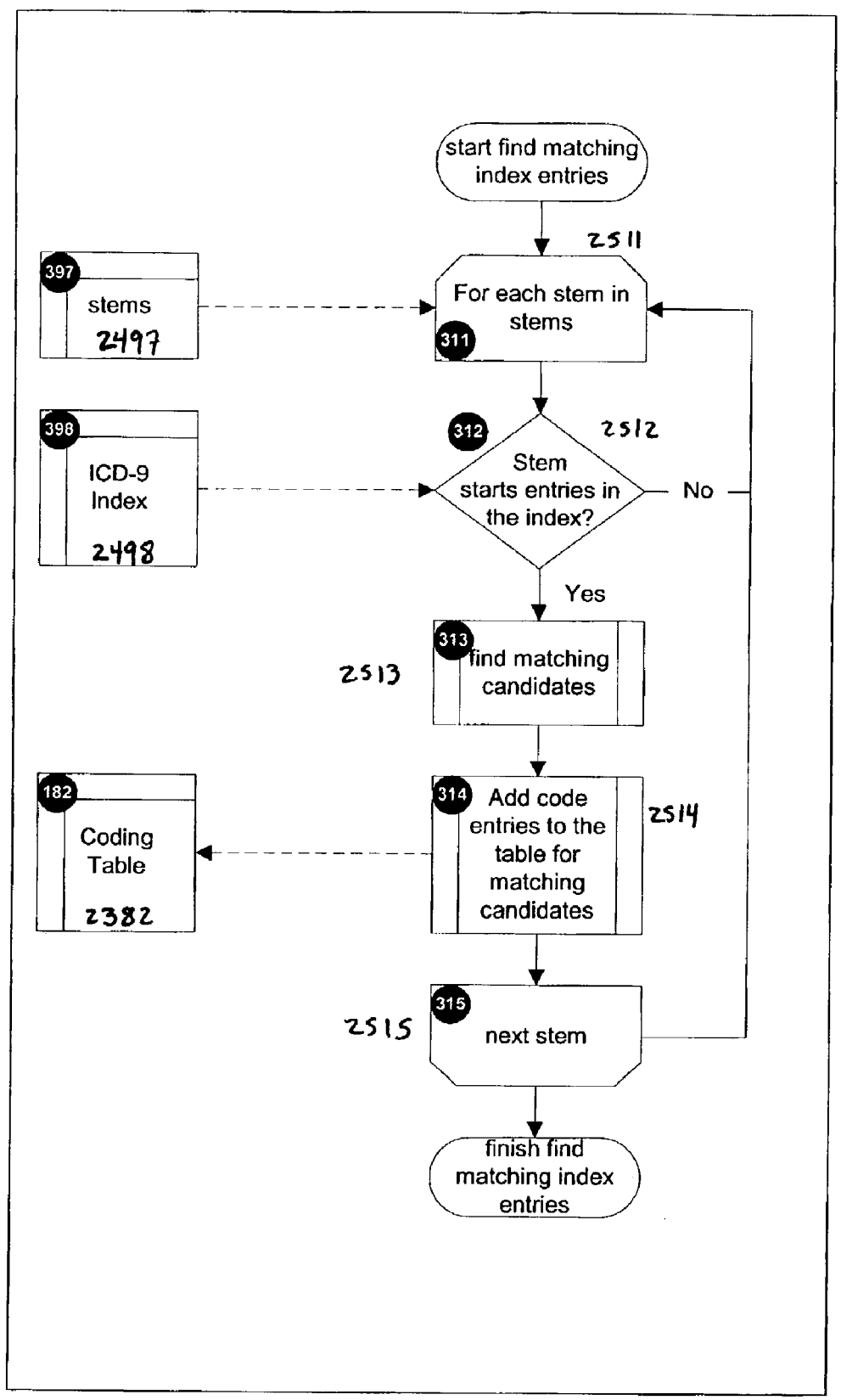
FIG. 25 is a flow diagram detailing steps for finding matching entries according to one embodiment of the invention.

FIG. 25 details the process of finding matching entries, step 2409 in the coding index lookup process depicted in FIG. 24. The process of finding matching entries may comprise a loop of steps 2511–2515 over the stem in the stems array 2497. Step 312 determines whether the stem starts one or more entries in the index 2498. If not, the loop over each stem may continue 2511. But if the instant stem starts one or more entries in the index 2498, the system may proceed to step 2513. In step 2513, matching candidates may be found in the index. The process of finding matching candidates is detailed in FIG. 26. In step 314, for each matched candidate, a code may be added to the coding table 2382. The loop may then continue 2515 if there are more stems.

Figure 26:
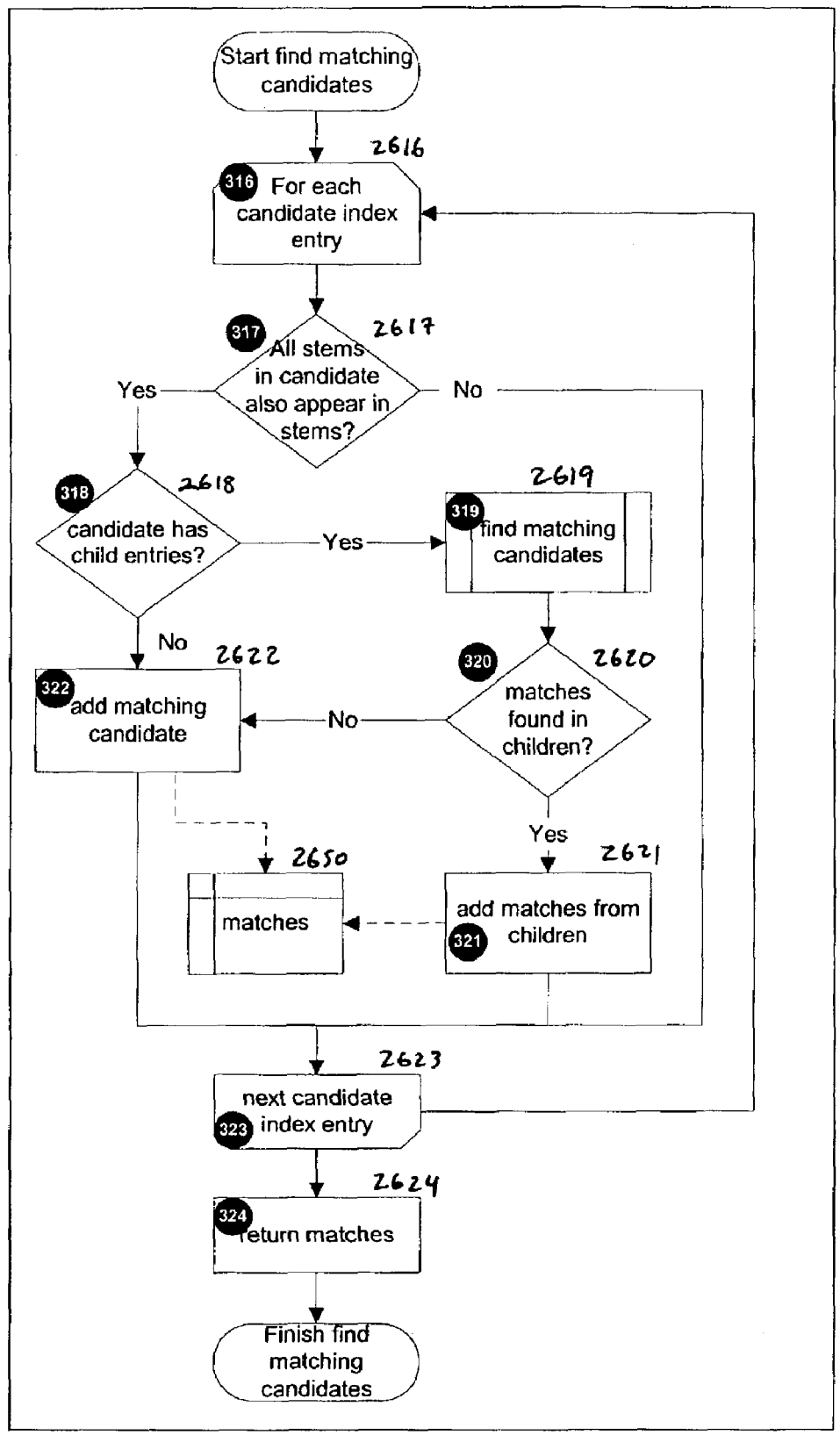
FIG. 26 is a flow diagram detailing process for finding candidate entries according to one embodiment of the invention.

FIG. 26 details the process of finding candidate entries. Candidate entries, which are entries that could potentially be matches, may be tested. If they match, they may be returned to the calling function. Steps 2616–2623 loop over each candidate index entry. Step 2617 determines whether all stems in the candidate entry also appear in the stems for the sentence. If so, the process may continue at step 2618. But if not, then the loop over the candidate index entries may continue 2623.

If all stems in the candidate entry also appear in the stems for the sentence as determined in step 2617, then step 2618 may determine whether the candidate index entry has subordinate (child) entries. If so, the process may continue at step 2619. If not, then the matching candidate may be added to a list of matches found 2650 in step 2622, and the loop over candidate index entries may continue 2623.

If the candidate index entry has subordinate entries, as determined by step 2618, then the matching candidates from the child entries may be found in step 2619 by a recursive call of this routine using the children as the new list of candidates. Step 2620 may determine whether there were matches found in the children. If not, the process may continue at step 2622 as described above. If there were matches found in the children, these may be added to the list of matches found 2650, and the loop over candidate index entries may continue 2623.

Finally, when the loop over candidate index entries is complete, the process returns the list of matches found 2650.

Figure 27:
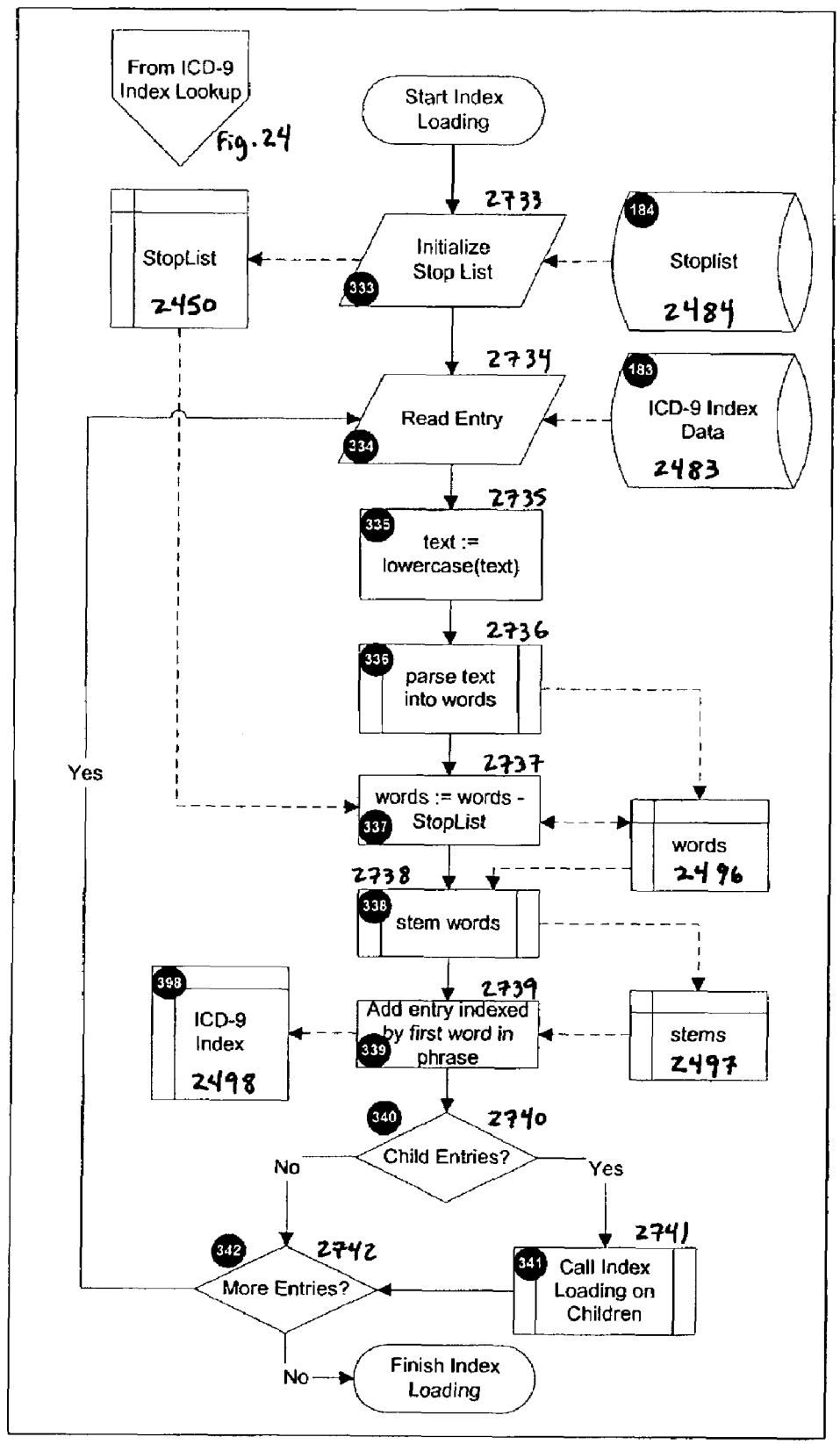
FIG. 27 is a flow diagram detailing a process for index loading according to one embodiment of the invention.
Figure 28:
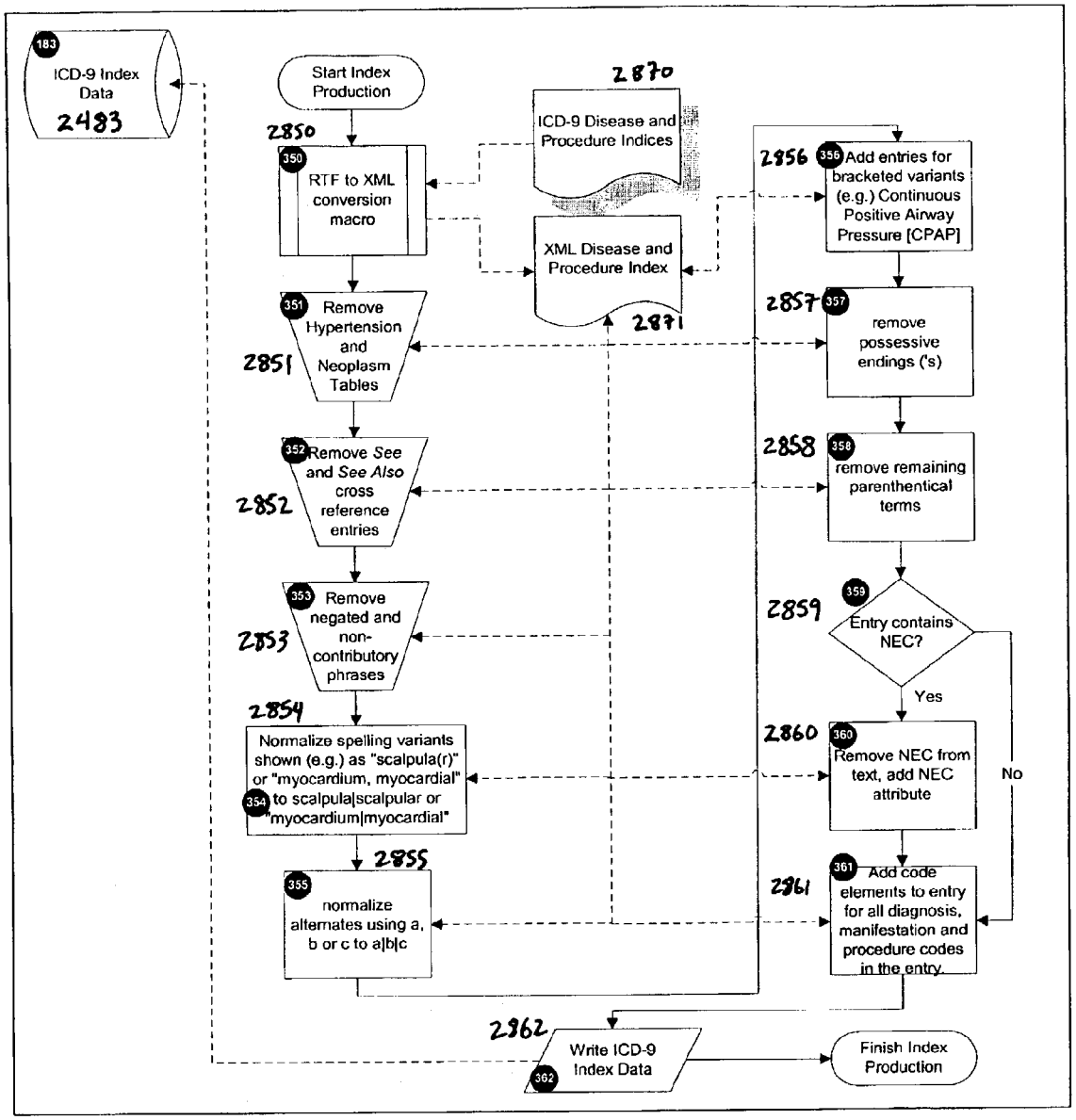
FIG. 28 is a flow diagram detailing a process for index data production according to one embodiment of the invention.

FIG. 27 details the process of index loading, part of step 2401, depicted in FIG. 24. The ICD-9 index data file 2483 generated as depicted in FIG. 28, is loaded as shown in FIG. 27. It should be noted that steps 2735–2738 in FIG. 28 are very similar to steps 2404–2408 in FIG. 24, depicting the ICD-9 index lookup process. These similarities ensure that the same things are being compared when phrases are looked up in the index.

In step 2733, the stop list 2450 may be loaded from storage 2484 into a hash table in memory. The stop list 2450 may contain a list of words that are not relevant when looking up phrases in the index. In step 2734, an entry may be read from the ICD-9 index data 2483. In step 2735, the text of the index entry may be converted to lower case. In step 2736, the text may be broken into words at white space and punctuation boundaries to create a list of words 2496. In step 2737, words appearing in both the list of words 2496 and the stop list 2450 may be removed from the list of words 2496. In step 2738, each word in the list 2497 may then be stemmed using an algorithmic stemmer, as described in the text accompanying FIG. 24, to provide a list of stem words 2497.

In step 2739, an entry may be added to the ICD-9 index 2498 using the first word in the phrase as the key for the entry. Step 2740 may determine whether there are child entries. If not, the method may continue at step 2742. If there are child entries, then in step 2741, the child entries may be added by calling this routine (as shown in FIG. 27) recursively, using the parent entry as the ICD-9 index 2498.

Step 2742 may determine whether there are more entries in the ICD-9 index data 2483 to process. If so, the process may loop back to step 2734, where the next entry is read. If not, then index loading may be complete.

FIG. 28 details the process of index data production. The index data may be prepared from published indices mapping conditions and procedures to codes in the ICD-9-CM. This is an editorial process that may be controlled by a human editor familiar with linguistic processing, and supported by a computer editor that supports global search and replace pattern matching. It should be noted that the process described below is only one method of index data production, but many other methods may be used with essentially similar results.

In step 2850, the ICD-9 disease and procedure indices 2870 may be converted from rich text format (RTF) to XML, to produce an XML disease and procedure index 2871. In step 2851, Hypertension and Neoplasm tables may be removed from the index 2871. In step 2852, cross reference entries may be removed from the index 2871. In step 2853, negated and non-contributory phrases may be removed from the index 2871. In step 2854, spelling variants may be normalized within the index 2871. In this step, words such as scalpula and scalpular may be replaced with scalpula-lscalpular and words such as myocardium and myocardial may be replaced with myocardiumlmyocardial.

In step 2855, alternates appearing as, for example, "a, b, or c" may be normalized in the index 2871 by replacement with alblc. In step 2856, entries for bracketed variants may be added to the index 2871. For example acronyms such as CPAP for Continuous Positive Airway Pressure may be added. In step 2857, possessive endings ("'s") may be removed from words in the index 2871. In step 2858, any remaining parenthetical terms may be removed from the index 2871.

Step 2859 determines whether a particular entry is not elsewhere classified, which is denoted as "NEC" in the disease and procedure indices 2870. If not, the system may proceed to step 2861. If the entry does contain an NEC designation, then in step 2860, the NEC may be removed from the text of the entry in the index 2871, and an NEC attribute added.

In step 2861, code elements may be added to an entry for all diagnosis, manifestation, and procedure codes in the entry. On completion, in step 2862, the index 2871 may be written as ICD-9 index data 2483.

Figure 29:
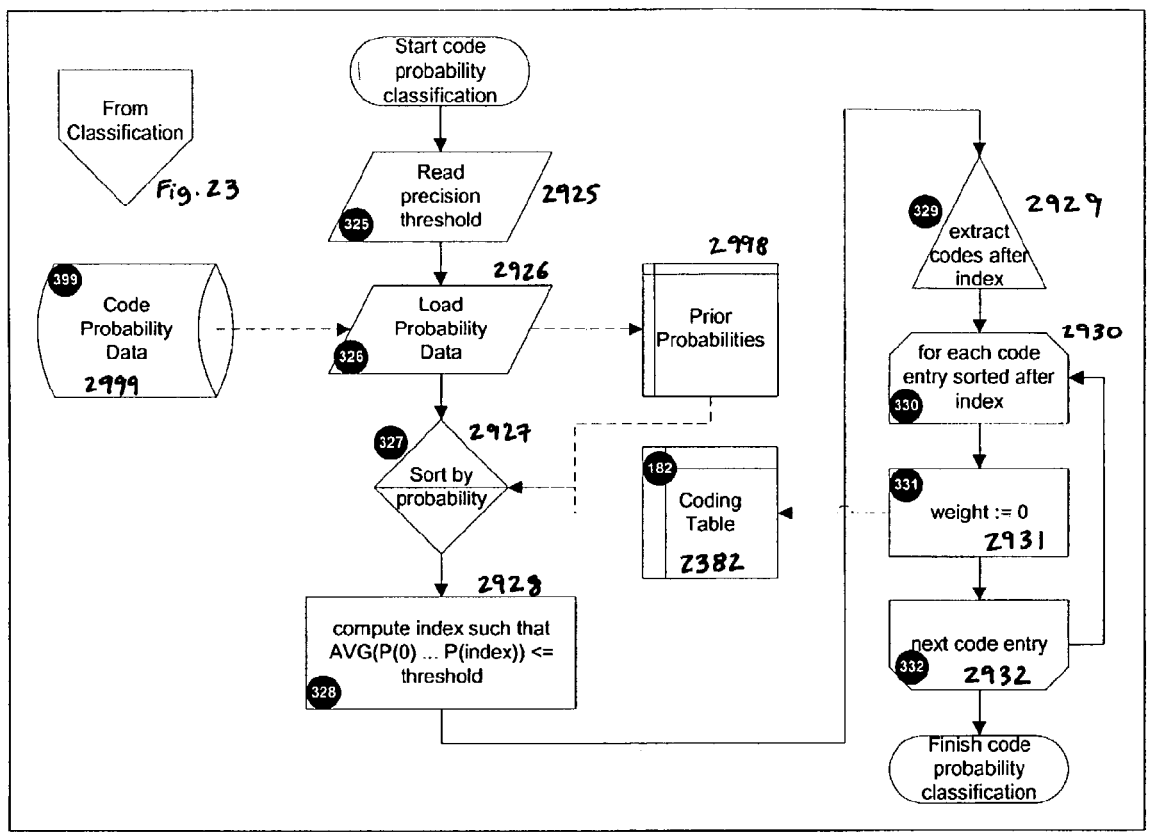
FIG. 29 is a flow diagram detailing a process for code probability classification according to one embodiment of the invention.

FIG. 29 details the process of code probability classification. Codes that are probably not correct may be filtered out by this process. The process may determine the likelihood that an entry in the coding table is correct using two pieces of information. First is the source of the coding entry. Second is the prior probability that the coding entry was correct in encounters that were coded manually and using the software.

In step 2925, the precision threshold may be read and set for the classifier from a client-specific data file. In step 2926, client specific probability results may be read from data file 2999 into a prior probability array 2998. In step 2927, the unique codes in the coding table 2382 may then be sorted by their prior probability. Zero may be used as the probability when the code does not appear in the data file(s). In step 2928, an index may be computed that specifies where codes may appear in the sorted list that would make the score for the document lower than the: threshold.

In step 2929, all entries whose code appears after the computed specified index in the sorted list may be extracted. Steps 2930–2932 loop over all extracted entries found in step 2929. In step 2931, the weight of each extracted entry is set to zero, which filters that entry. The process is complete on completion of the loop.

Figure 30:
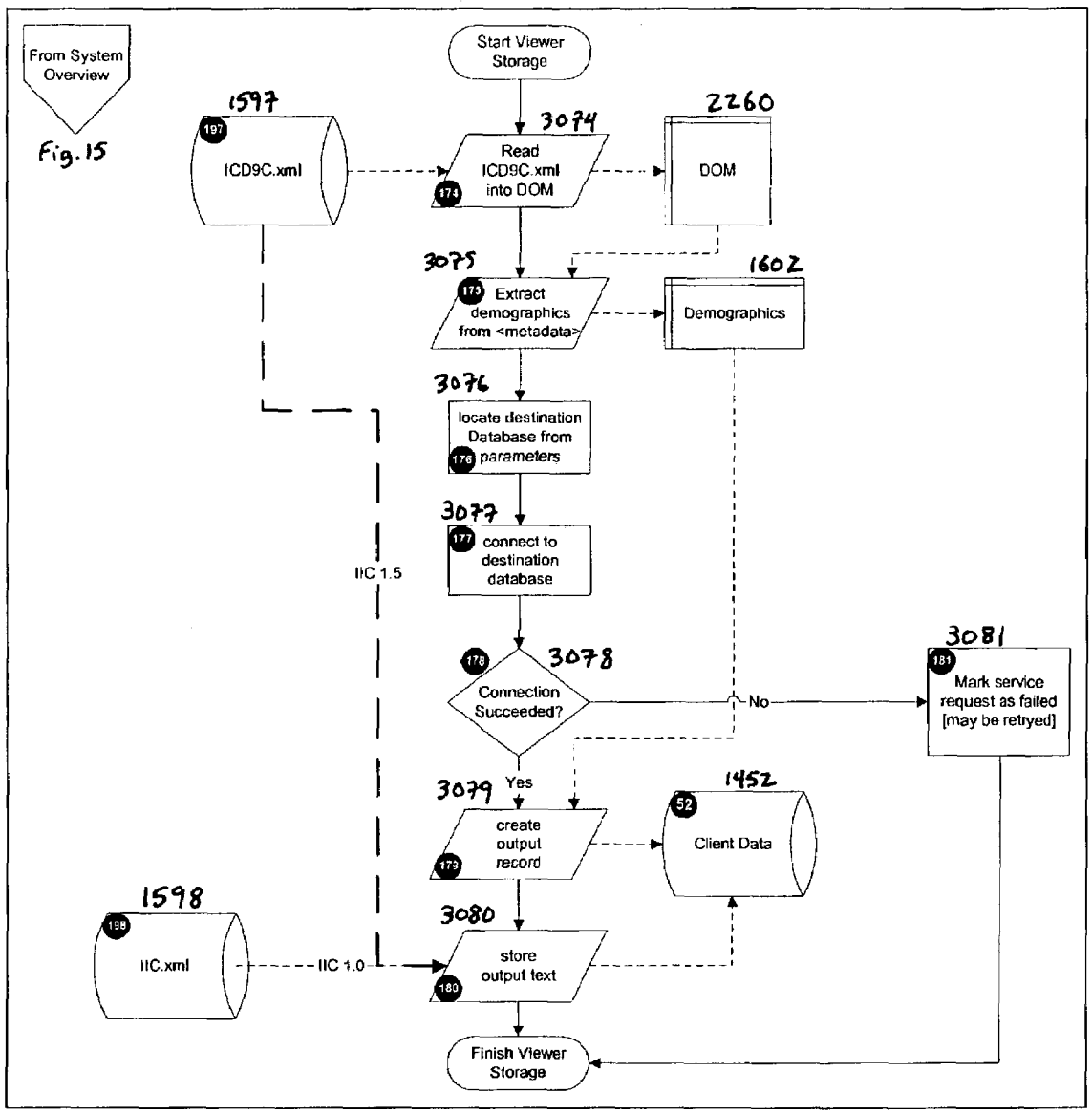
FIG. 30 is a flow diagram detailing a process for storing results in the client database according to one embodiment of the invention.

FIG. 30 details the process of storing results in the client database. The source document 1597 may be read into a DOM in memory 2260 in step 3074. In step 3075, demographics and document metadata may be extracted from the metadata element of the document using an XPath expression to create a demographics array 1602. Details about XPath can be found in James Clark et al., *XML Path Language (XPath)* Version 1.0, W3C (Nov. 16, 1999), incorporated herein by reference.

In step 3076, the destination database may be located from request specific parameters. In step 3077, a connection to the destination database may be made. Step 3078 may determine whether the connection has succeeded. If so, the process may continue at step 3079. If not, the service request may be marked as failed, and may be returned to the calling function.

If connection to the destination database is successful, then in step 3079, an output record may be created using the metadata in the client database 1452. In step 3080, the output XML document may be stored in the database 1452. In one embodiment, the output XML document may be read from the IIC file 1598. Preferably, however, the output XML document is read from the ICD9C file 1597. The service request thus succeeds, and the process returns to the calling function.

While the invention has been described in combination with embodiments thereof, many alternatives, modifications, and variations will be apparent to those skilled in the art in light of the foregoing description. Accordingly, the invention is intended to embrace all such alternatives, modifications, and variations as fall within the spirit and broad scope of the appended claims. All patent applications, patents, and other publications sighted herein are incorporated by reference in their entirety.

What is claimed is:

1. A method for coding at least one medical record having a format and textual content using a computer, said computer associated with at least one data storage device configured to store each said medical record, the method comprising the steps of:

receiving medical documents for coding from multiple clients, wherein the medical documents from each client are received in client-specific directories on the data storage device;

normalizing the format of the medical documents into a predetermined format, wherein the predetermined format is determined based upon information in the medical documents or based upon from which directory in the date storage device the medical documents are received;

normalizing the textual content of the medical documents;

identifying coded items in the textual content of the medical documents, wherein the coded items are identified based on a comparison of the textual content in the medical documents and a standardized classification system, the standardized classification system selected from the group consisting of: SNOMED, ICD-9, ICD-10, ICD-9-CM, ICD-10-CM, and CPT;

filtering the coded items, wherein the coded items are filtered based on a probabilistic filter, where the probabilistic filter includes:

determining a precision threshold for each medical document;

gathering client specific probability data;

creating a probability array from the client specific probability data;

sorting probability codes from a coding table;

creating a coding index based on the client specific probability data and the sorted probability codes, where the coding index is used to determine the location of the medical document in relation to the precision threshold; and extracting probability codes located after the precision threshold in the coding index; and creating a coded document, wherein the coded document contains text justifying the filtered coded items, and the filtered coded items.

2. The method of claim 1 further comprising the step of identifying at least one element to be coded based upon a location of the at least one element within the medical records.

3. The method of claim 1, further comprising the step of converting the coded document into a format compatible with viewing software.

4. The method of claim 1, further comprising the step of converting the medical document to XML format.

5. A system for coding at least one medical record comprising:
- a computer having a central processing unit and being configured to normalize the at least one medical record to conform to a predetermined format;
- a coding engine associated with the central processing unit, the coding engine associated with at least one medical standard and being configured to identify at least one element to be coded within the at least one normalized medical record;
- at least one data storage device associated with the computer, the at least one data storage device configured to store each medical record;
- the computer further configured to select the coding engine based on the predetermined format the computer configured to create a coded document, wherein the coded document contains text justifying the filtered coded items, and the filtered coded items;
- wherein the predetermined format is determined from information in the medical record from which directory on the computer the medical records are stored;
- and wherein the at least one coding engine is further configured to assign coded items based on a probabilistic filter where the probabilistic filter includes:
  - determining a precision threshold for each medical document;
  - gathering client specific probability data;
  - creating a probability array from the client specific probability data;
  - sorting probability codes from a coding table;
  - creating a coding index based on the client specific probability data and the sorted probability codes, where the coding index is used to determine the location of the medical document in relation to the precision threshold; and
  - extracting probability codes located after the precision threshold in the coding index.

6. The system of claim 5, wherein the coding engine is a Gabriele engine.

7. The system of claim 5, further comprising an application for post-processing the coded document, the post-processing application configured to convert the coded document into a format compatible with viewing software.

8. The system of claim 5, wherein the computer is further configured to convert said normalized medical record into XML format.

9. The system of claim 5, wherein the coding engine provides ICD-9-CM codes.

10. A method for coding at least one medical record using a computer, the computer associated with at least one data storage device configured to store each medical record, the method comprising the steps of:
- normalizing the at least one medical record to conform with XML format;
- selecting a coding engine based on the XML format, the coding engine associated with at least one medical terminology standard, the at least one medical terminology standard selected from the group consisting of: SNOMED, ICD-9, ICD-10, ICD-9-CM, ICD-10-CM, and CPT;
- identifying at least one element to be coded within the at least one normalized medical record using a probabilistic filter, where the probabilistic filter includes:
  - determining a precision threshold for each medical document;
  - gathering client specific probability data;
  - creating a probability array from the client specific probability data;
  - sorting probability codes from a coding table;
  - creating a coding index based on the client specific probability data and the sorted probability codes, where the coding index is used to determine the location of the medical document in relation to the precision threshold; and
  - extracting probability codes located after the precision threshold in the coding index, and where
- the at least one element comprising a word or a phrase, the word or phrase relating to an ailment, an allergy, a medical condition, a diagnosis, a treatment plan, or a medication;
- assigning a medical code to the at least one identified element, the medical code relating to the at least one medical terminology standard; and
- creating a coded medical record containing the medical code adjacent to each the identified element, the coded medical record being in XML format.

\* \* \* \* \*